(12) United States Patent
Khamar et al.

(10) Patent No.: US 9,029,567 B2
(45) Date of Patent: *May 12, 2015

(54) HYPOGLYCEMIC COMPOUNDS

(75) Inventors: Bakulesh Mafatlal Khamar, Ahmedabad (IN); Chandan Singh, Ahmedabad (IN); Rajiv Indravadan Modi, Ahmedabad (IN)

(73) Assignee: Cadila Pharmaceuticals Limited, Ahmedabad (IN)

(*) Notice: Subject to any disclaimer, the term of this patent is extended or adjusted under 35 U.S.C. 154(b) by 26 days.

This patent is subject to a terminal disclaimer.

(21) Appl. No.: 13/639,596

(22) PCT Filed: Apr. 1, 2011

(86) PCT No.: PCT/IB2011/051407
§ 371 (c)(1),
(2), (4) Date: Feb. 12, 2013

(87) PCT Pub. No.: WO2011/125011
PCT Pub. Date: Oct. 13, 2011

(65) Prior Publication Data
US 2013/0150578 A1    Jun. 13, 2013

(30) Foreign Application Priority Data
Apr. 5, 2010 (IN) .......... 1130/MUM/2010

(51) Int. Cl.
C07D 209/00 (2006.01)
C07D 473/04 (2006.01)
A61K 31/4985 (2006.01)
C07D 209/52 (2006.01)
C07D 401/04 (2006.01)
C07D 401/14 (2006.01)
C07D 403/12 (2006.01)
C07D 471/04 (2006.01)
C07D 487/04 (2006.01)
C07D 403/14 (2006.01)

(52) U.S. Cl.
CPC .......... *C07D 473/04* (2013.01); *A61K 31/4985* (2013.01); *C07D 209/52* (2013.01); *C07D 401/04* (2013.01); *C07D 401/14* (2013.01); *C07D 403/12* (2013.01); *C07D 471/04* (2013.01); *C07D 487/04* (2013.01); *C07D 403/14* (2013.01)

(58) Field of Classification Search
CPC ..................................................... C07D 473/04
See application file for complete search history.

(56) References Cited

U.S. PATENT DOCUMENTS

2009/0137457 A1    5/2009    Harbeson

FOREIGN PATENT DOCUMENTS

WO    WO 2010029422 A1 *    3/2010

OTHER PUBLICATIONS

Tsai et al., "Rational design and synthesis of potent and long-lasting glutamic acid-based dipeptidyl peptidase IV inhibitors," Bioorganic & Medicinal Chemistry Letters, 2009, vol. 19, Issue 7, pp. 1908-1912.
Gupta et al., "Emerging Drug Candidates of Dipeptidyl Peptidase IV (DPP IV) Inhibitor Class for the Treatment of Type 2 Diabetes," Current Drug Targets, 2009, vol. 10, pp. 71-87.
PCT/IB2011/051407 International Search Report dated Aug. 9, 2011.

* cited by examiner

*Primary Examiner* — Noble Jarrell
*Assistant Examiner* — John S Kenyon
(74) *Attorney, Agent, or Firm* — Pepper Hamilton LLP

(57) ABSTRACT

The present invention relates to novel hypoglycemic compounds of formula (1) and pharmaceutically acceptable salts thereof. The invention relates to novel amino acid derivatives of the formula (1), wherein, A is amino acid B is peptide bond R-NH- wherein R is defined in the specification.

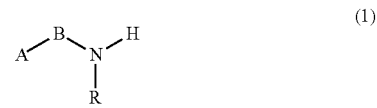

8 Claims, 2 Drawing Sheets

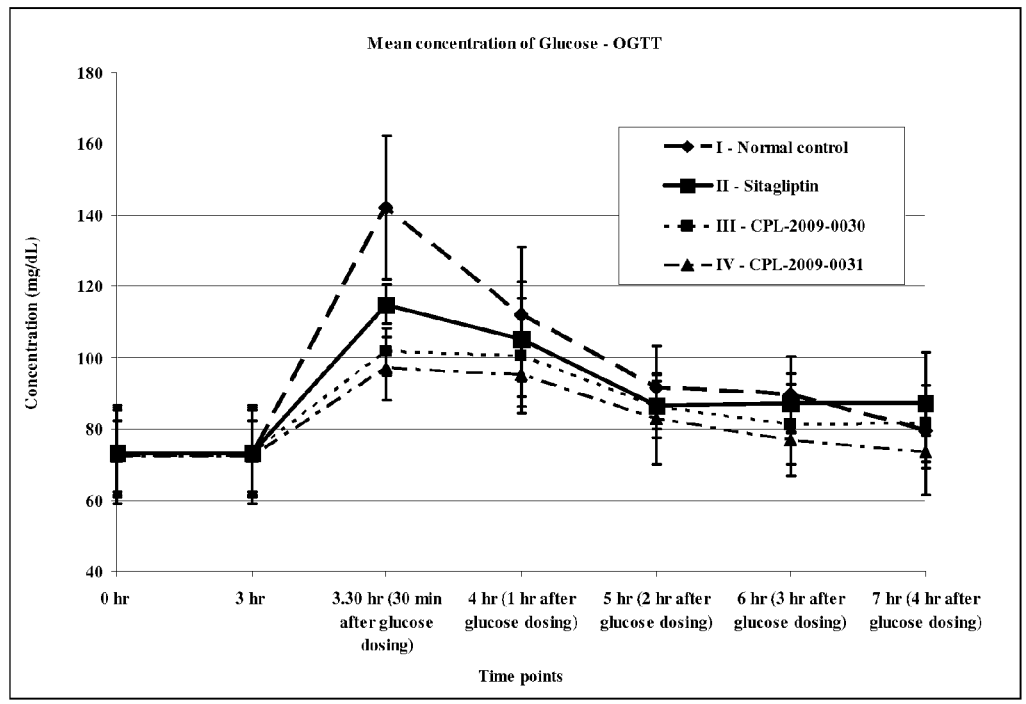
Figure: 01
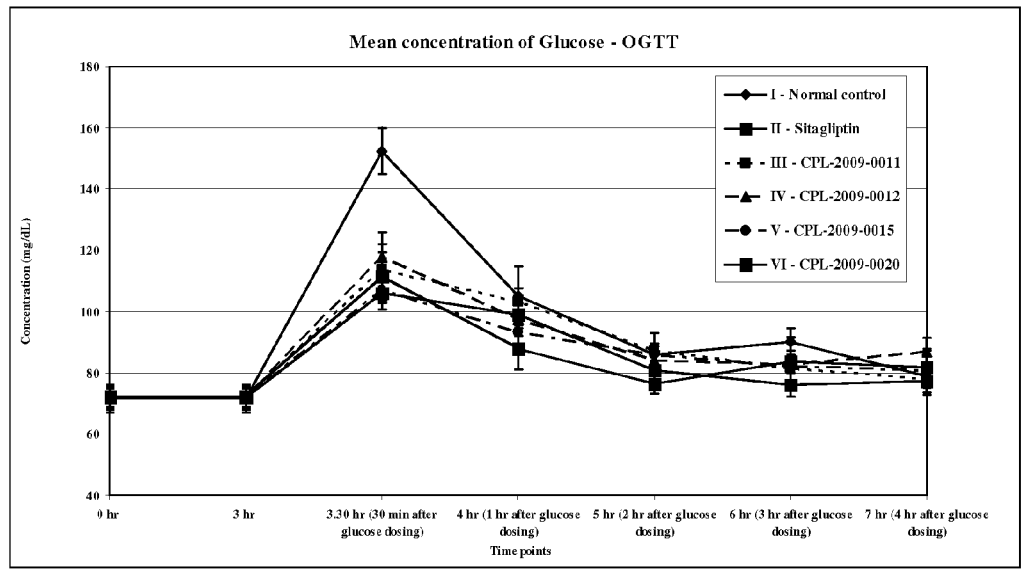
Figure: 02

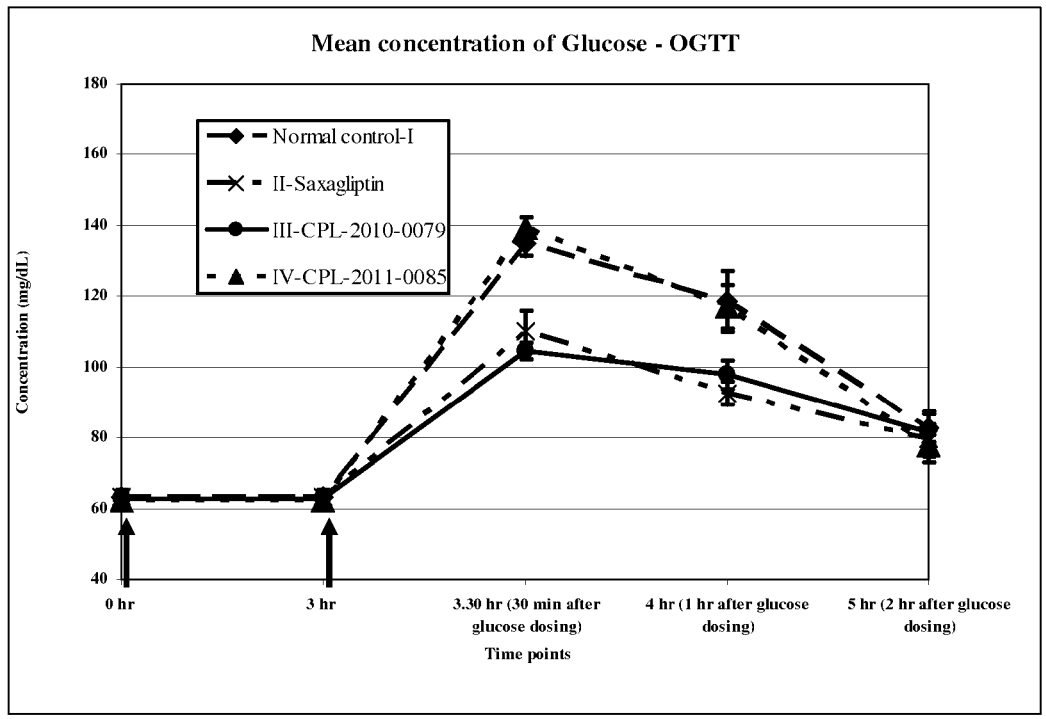
Figure: 03
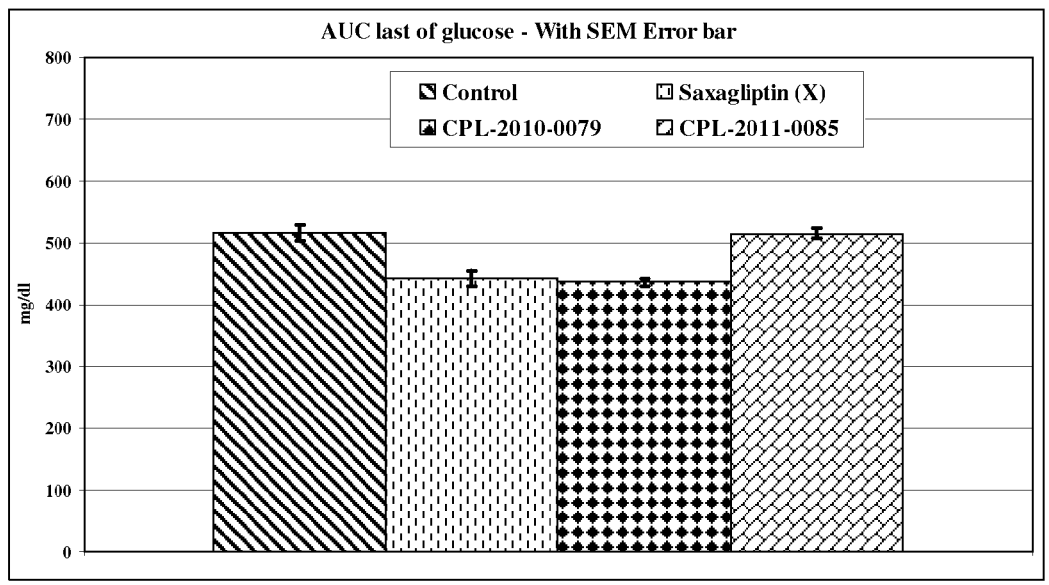
Figure: 04

HYPOGLYCEMIC COMPOUNDS

This application is the U.S. National Stage filing under 35 U.S.C. 0371 of International Application Serial No. PCT/IB2011/051407 filed Apr. 1, 2011, which claims priority to Indian Application No. 1130/MUM/2010 filed Apr. 5, 2010, each of which is incorporated herein by reference in its entirety.

FIELD OF INVENTION

The present invention is directed to novel hypoglycemic compounds of formula I and pharmaceutically acceptable salts thereof. The invention relates to novel amino acid derivatives of the formula I,

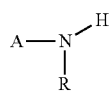

Formula 1 wherein,
A is amino acid,
R-NH- wherein R is defined in the specification.

BACKGROUND OF INVENTION

Diabetes mellitus (DM) is a group of diseases characterized by high levels of blood glucose resulting from defects in insulin production, insulin action, or both. The term diabetes mellitus describes a metabolic disorder of multiple aetiology characterized by chronic hyperglycaemia with disturbances of carbohydrate, fat and protein metabolism. The metabolism disturbance effect is resulting from defects in insulin secretion, insulin action, or both. The effects of diabetes mellitus include long-term damage, dysfunction and failure of various organs.

There are at least seven different classes of agents used as monotherapy, or in combinations for the treatment of diabetes mellitus. These include metformin, sulphonylureas, meglinitides, alpha-glucosidase inhibitors, thiazolidinediones, glucagon like peptide-1 agonists and insulin. Many conventional agents frequently exhibit reduced efficacy over time, leading to inadequate glycaemic control. Several of these agents are also associated with adverse effects that include weight gain, hypoglycemia and gastrointestinal distress. There is a need therefore, for alternative therapies that can overcome the limitations associated with conventional anti-hyperglycemic medications.

The conventional agents used to treat type 2 diabetes frequently exhibit reduced efficacy over time leading to inadequate glycaemic control and are also associated with adverse effects. Hence, there is a need for alternative therapies that can overcome the limitations associated with conventional antidiabetic agents.

DESCRIPTION OF DRAWING

FIG. 1: In vivo screening results of CPL-2009-030 & CPL-2009-031.
FIG. 2: In vivo screening results of CPL-2009-011, CPL-2009-012, CPL-2009-015 & CPL-2009-020.
FIG. 3: In vivo screening results of CPL-2010-079, CPL-2011-085
FIG. 4: In vivo screening results (AUC) of CPL-2010-079, CPL-2011-085

OBJECT OF THE INVENTION

An object of this invention is to provide novel hypoglycemic compounds of formula I and its pharmaceutically acceptable salts thereof.

Another object of this invention is to provide a process for the preparation of the novel hypoglycemic compounds of formula I.

Yet another object of the invention is to provide novel hypoglycemic compounds which react with DPP IV enzyme.

DESCRIPTION OF INVENTION

The synthesized compounds are potential candidates for the treatment of metabolic disorder associated with diabetes mellitus. We disclose herein a series of novel compounds that are potential hypoglycemic compounds. The invention relates to novel amino acid derivatives of the formula I,

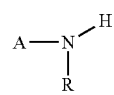

Formula 1 wherein,
A is amino acid,
R-NH- wherein R-NH- is a group of formulae 2 to 6 which is derived from R-NH$_2$ which is a DPP IV inhibitor having primary amine,

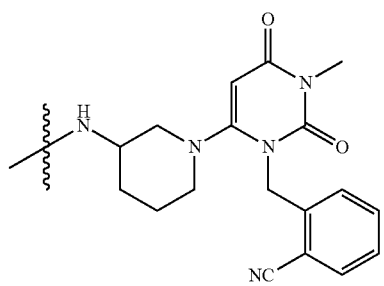

Formula 2

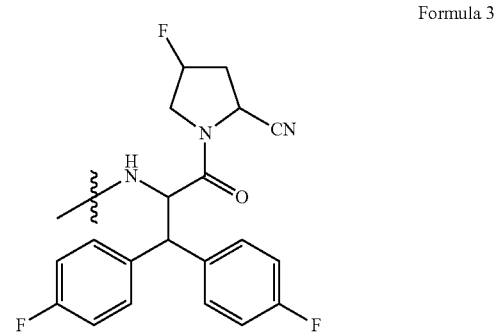

Formula 3

-continued

Formula 4

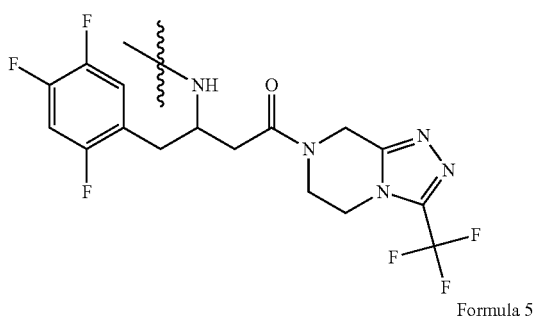

Formula 5

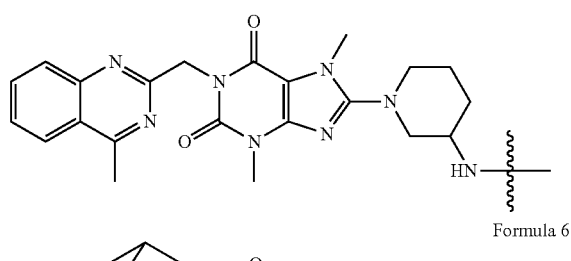

Formula 6

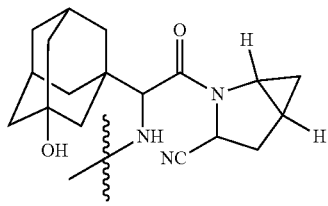

The compound of formula 2-6 are chemically named as, 2-({6-[(3R)-3-substituted-aminopiperidin-1-yl]-3-methyl-2,4-dioxo-3,4-dihydropyrimidin-1(2H)-yl}methyl)-benzonitrile (formula 2);

1-[2-substituted-amino-3,3-bis-(4-fluoro-phenyl)-propionyl]-4-fluoro-pyrrolidine-2-carbonitrile (formula 3);

(2R)-2-substituted-amino-4-oxo-4-[3-(trifluoromethyl)-5,6-dihydro[1,2,4]triazolo[4,3- a]pyrazin-7(8H)-yl]-1-(2,4,5-trifluorophenyl)butan (formula 4);

8-[(3R)-3-2-substituted-aminopiperidin-1-yl]-7-(but-2-yn-1-yl)-3-methyl-1-[(4- methylquinazolin-2-yl)methyl]-3,7-dihydro-1H-purine-2,6-dione (formula 5);

(1S,3S,5S)-2-[(2S)-2-2-substituted-amino-2-(3-hydroxy-1-adamantyl)acetyl]-2- azabicyclo-[3.1.0]-hexane-3-carbonitrile (formula 6); and salts thereof.

The title compounds were synthesized by reaction of carboxylic group of an amino acid (A-OH) and the amino group of R-NH₂ wherein R-NH- has one of formulae 2-6 by the scheme 1.

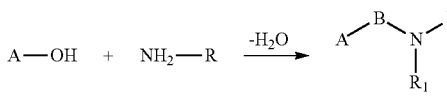

Formula 1 wherein
A is amino acid,
R-NH- wherein R-NH- is together a group of formulae 2 to 6 which is derived from a DPP IV inhibitor having primary amine (i.e. R-NH₂).

The process disclosed herein is not limited to the preparation of specific compounds as prepared herein but is described the general state of art in order to prepare the compounds of present invention. The compounds of formula 2-6 are prepared by the process as known in literature. The scope of invention also includes compound which are selected from the group consisting of the compounds of formula 2-6 or its pharmaceutically acceptable salts thereof to prepare similarly set of other compounds.

The present invention is directed to the use of the compounds disclosed as hypoglycemic activity. The following synthesized compounds are useful as hypoglycemic compound for a patient such as a mammal in need of such diabetic treatment comprising the administration of an effective amount of the compound.

The following examples serve to illustrate the present invention directed to provide novel hypoglycemic compounds of formula I and its pharmaceutically acceptable salts thereof having hypoglycemic activity in humans and animals comprising the pharmaceutical composition combining a compound of the present invention with a pharmaceutical carrier or diluent.

EXAMPLE 1

Tert-Butoxycarbonylamino-acetic acid (0.33 gms, 0.0018 mole) was dissolved in dichloromethane (20 ml) and added in dicyclohexyl dicarbodiimide (0.51 gm, 0.0025 M) at 0 0 C. The reaction mixture was stirred for 10 minutes. 3-Amino-1-(3-trifluoromethyl-5,6,7,8-tetrahydro-[1,2,4]triazolo[4,3-a]pyridin-7-yl)-4-(2,4,5-trifluoro-phenyl)-butan-1-one (Formula 4) (0.59 gm, 0.00123 M) was added at 0 0 C and stirred. dicyclohexyl urea was removed After the reaction mixture being stirred. The reaction mixture was filtered and filtrate was concentrated under vacuum. The residue was purified by column chromatography to yield {[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-methyl}-carbamic acid tert-butyl ester (Formula 7). (Yield: 0.62 gm, 89%)

Scheme: 01

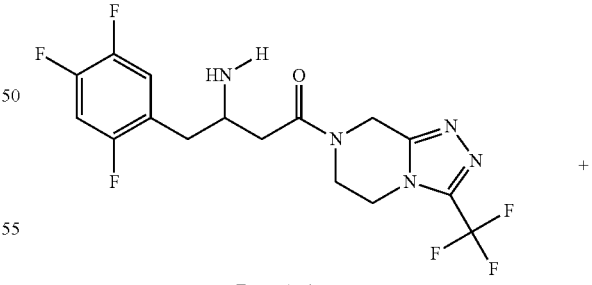

Formula 4
3-Amino-1-(3-trifluoromethyl-5,6,7,8-tetrahydro-[1,2,4]trizolo[4,3-a]pyridin-7-yl)-4-(2,4,5-trifluoro-phenyl)-butan-1-one

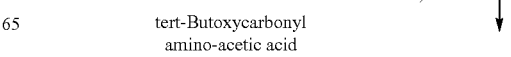

tert-Butoxycarbonyl amino-acetic acid

Dichloro Methane, DCC, 0° C.

-continued

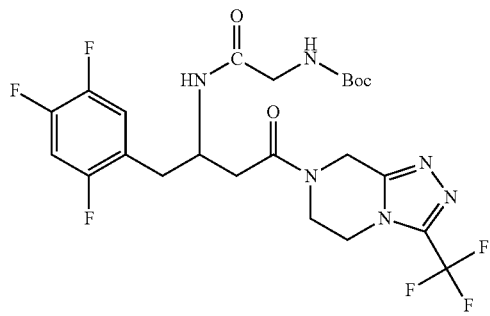

Formula 7
{[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-methyl}-carbamic acid tert-butyl ester

EXAMPLE 2

Scheme: 02

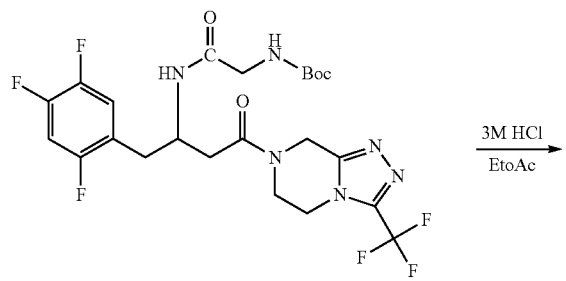

Formula 7
{[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-methyl}-carbamic acid tert-butyl ester

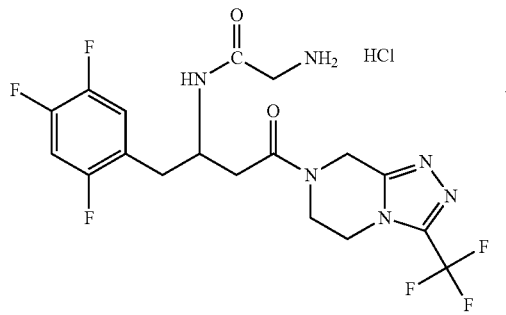

Formula 8
Hydrochloride salt of 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-acetamide {[3-Oxo-1-(2,4,5-trifluoro-benzyl)-3-(3-trifluoromethyl-5,6-dihydro-8H-[1,2,4]triazolo-[4,3-a]-pyrazin-7-yl)-propylcarbamoyl]-methyl}-carbamic acid tert-butyl ester (Formula 7) (0.52 gms, 0.0009 mole) was dissolved in EtoAc and stirred at room temperature. 3M HCl-EtoAc (3 ml) was added to the reaction mixture and stirred at room temperature. The reaction mass was concentrated under vacuum to yield 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-acetamide Hydrochloride (Formula 8). (0.447 gm, 96%)

EXAMPLE 3

Analogously to example 1 the compound, {3-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propyl-carbamoyl]-butyl}-carbamic acid tert-butyl ester (Formula 9) is prepared by the reaction of compound having formula 4 (0.59 gm) and 2-tert-Butoxycarbonyl amino-4-methyl pentanoic acid (0.43 gm). The reaction mixture is concentrated under vacuum and purified by column chromatography. (Yields 0.62 gm, 81%)

Formula 9

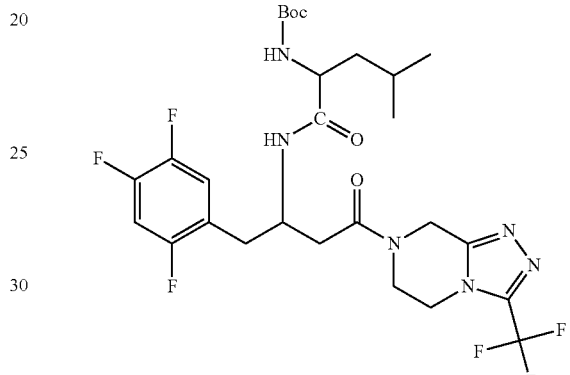

{3-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-butyl}-carbamic acid tert-butyl ester Formula 10

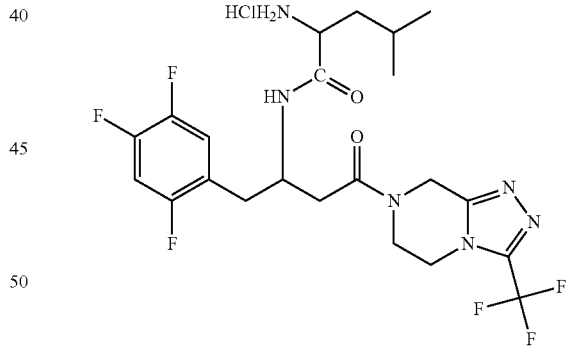

2-Amino-4-methyl-pentanoic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride

EXAMPLE 4

Analogously to example 2 the compound, [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride (Formula 10) is prepared by saltification of the compound of formula 9 (0.52 gm) using hydrochloric acid. (Yield: 0.45 gm, 96%).

EXAMPLE 5

Analogously to example 1 the compound, {2-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propyl-carbamoyl]-butyl}-carbamic acid tert-butyl ester (Formula 11) is prepared by the reaction of compound having formula 4 (0.5 gm) and 2-tert-Butoxycarbonyl amino-3-methyl pentanoic acid (0.283 gm). The residue is purified by column chromatography. (Yields 0.47 gm, 62.7%)

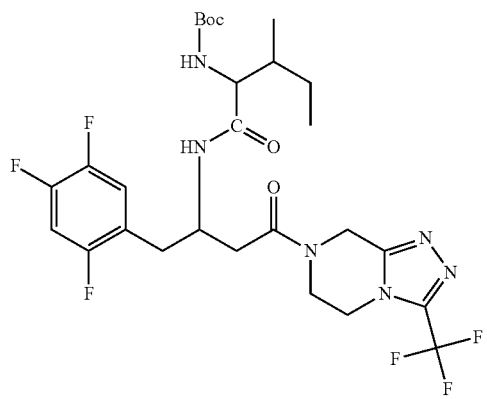

Formula 11

{2-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-butyl}-carbamic acid tert-butyl ester

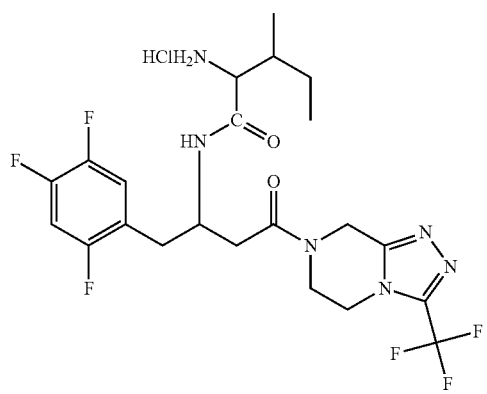

Formula 12

2-Amino-3-methyl-pentanoic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride

EXAMPLE 6

Analogously to example 2, 2-Amino-3-methyl-pentanoic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride (Formula 12) is prepared by saltification of the compound of formula 11 (0.44 gm) using hydrochloric acid at room temperature. (Yield=0.39 gm, 98.73%).

EXAMPLE 7

Analogously to example 1 the compound, 2-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carboxylic acid tert-butyl ester (Formula 13) is prepared by the reaction of compound having formula 4 (0.5 gm) and Pyrrolidine-1,2-dicarboxylic acid 1-tert-butyl ester (0.464 gm). The residue was purified by column. (Yield=0.42 gm, 89%)

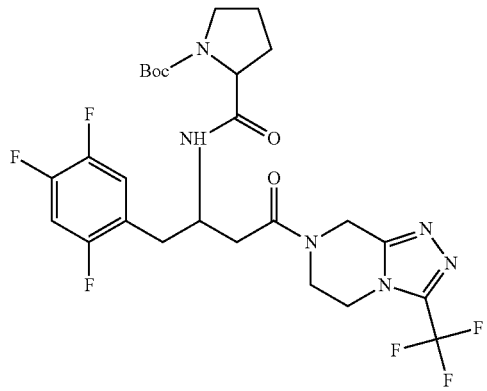

Formula 13

2-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carboxylic acid tert-butyl ester

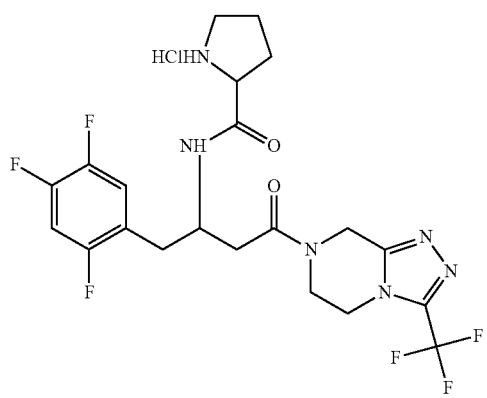

Formula 14

Pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide

EXAMPLE 8

Analogously to example 2, Pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide Hydrochloride (Formula 14) is prepared by saltification of the compound of formula 13 (0.55 gm) using hydrochloric acid. (0.49 gm, Yield=81%)

EXAMPLE 9

Analogously to example 1 the compound, {2-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-propyl}-carbamic acid tert-butyl ester (Formula 15) is prepared by the reaction of compound having formula 4 (1 gm) and 2-tert-Butoxycarbonylamino-3-methyl-butyric acid (0.59 gm). (Yield: 1.2 gm, 82%)

Formula 15

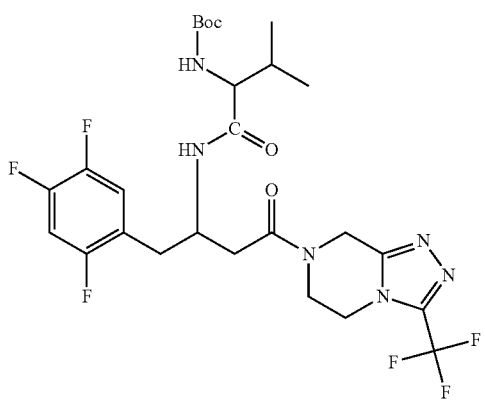

{2-Methyl-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-propyl}-carbamic acid tert-butyl ester Formula 16

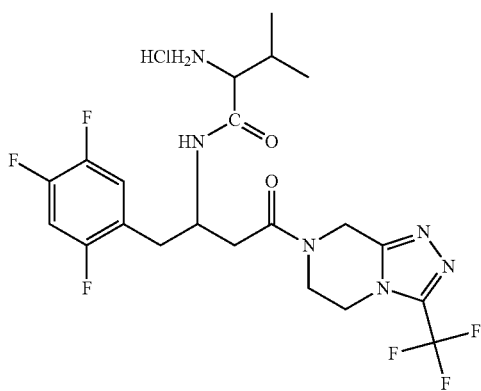

2-Amino-3-methyl-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-butyramide Hydrochloride

EXAMPLE 10

Analogously to example 2, 2-Amino-3-methyl-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-butyramide Hydrochloride (Formula 16) is prepared by saltification of the compound of formula 15 (1.2 gm) using hydrochloric acid. (Yield: 1.03 gms, 95%)

EXAMPLE 11

Analogously to example 1, {1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Formula 17) is prepared by the reaction of compound having formula 4 (1 gm) and 2-tert-Butoxycarbonyl amino-propionic acid (0.464). The residue was purified by silica gel chromatography using $CH_2Cl_2$/MeOH (9.8: 0.2) as an eluent. (Yield: 1.3 gm, 90%)

Formula 17

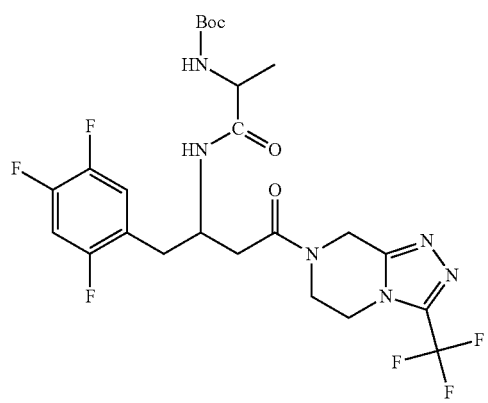

{1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester Formula 18

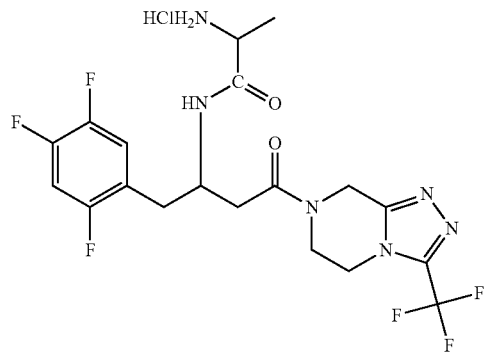

2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide Hydrochloride

EXAMPLE 12

Analogously to example 2, 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide Hydrochloride (Formula 18) is prepared by saltification of the compound of formula 17 (0.6 gm) using hydrochloric acid. The hydrochloride salt was dissolved in saturated aq. $NaHCO_3$ and was extracted with EtoAC (50 ml×3). The combined EtoAC layers were dried over $Na_2SO_4$ and were concentrated under vacuum to give the title compound. (Yield: 0.454 gm, 89%)

EXAMPLE 13

Analogously to example 1, {2-(3-Benzyloxy-phenyl)-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Formula 19) is prepared by the reaction of compound having formula 4 (0.49 gm) and 3-(3-Benzyloxy-phenyl)-2-tert-butoxycarbonylamino-propionic acid (0.44 gm). The residue was purified by silica gel chromatography using $CH_2Cl_2$/MeOH (9.25: 0.75) as an eluent. (Yield=0.62 gm, 68%)

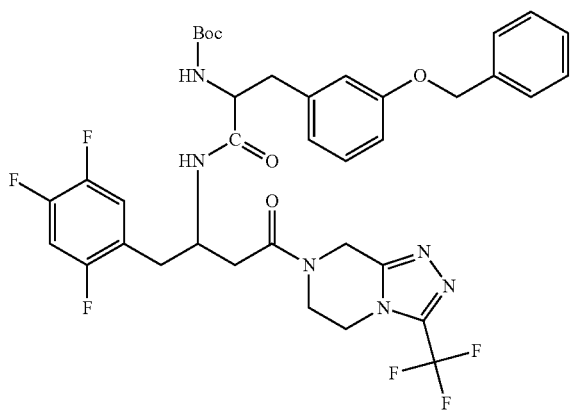

Formula 19

{2-(3-Benzyloxy-phenyl)-1-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester

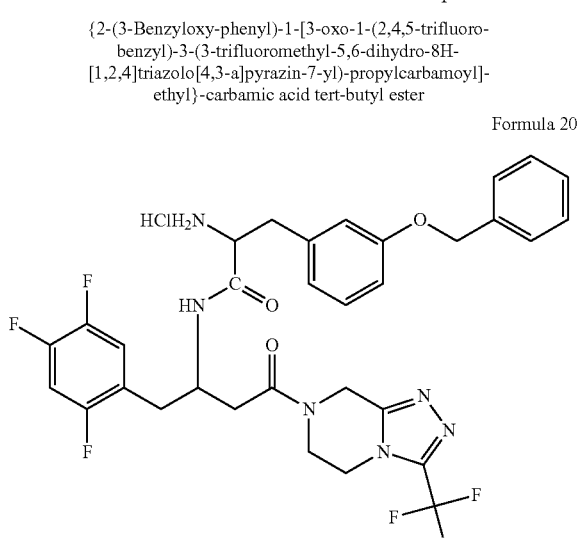

Formula 20

2-Amino-3-(3-benzyloxy-phenyl)-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide Hydrochloride

EXAMPLE 14

Analogously to example 2, 2-Amino-3-(3-benzyloxy-phenyl)-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide Hydrochloride (Formula 20) (0.5 gm) is prepared by saltification of the compound of formula 19 using hydrochloric acid at room temperature. (Yield=0.43 gm, 93.48%)

EXAMPLE 15

Analogously to example 1, {1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-2-phenyl-ethyl}-carbamic acid tert-butyl ester (Formula 21) is prepared by the reaction of compound having formula 4 (0.5 gm) and 2-tert-Butoxycarbonylamino-3-phenyl-propionic acid (0.325 gm). The residue was purified by silica gel chromatography using CH$_2$Cl$_2$/MeOH (9.5: 0.5) as an eluent. (Yield=0.49 gm, 61.25%)

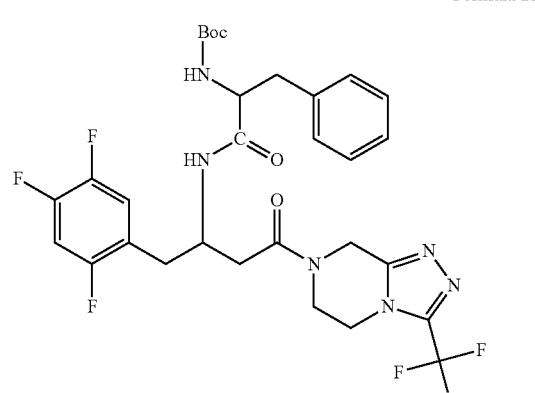

Formula 21

{1-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-2-phenyl-ethyl}-carbamic acid tert-butyl ester

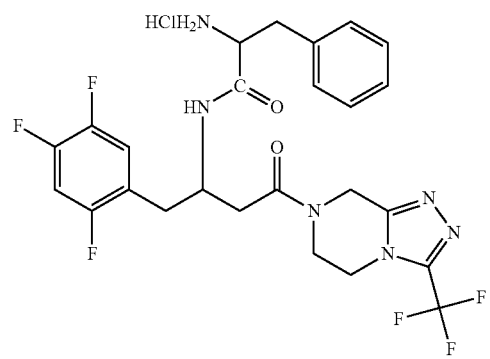

Formula 22

2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-3-phenyl-propionamide Hydrochloride

EXAMPLE 16

Analogously to example 2, 2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-3-phenyl-propionamide Hydrochloride (Formula 22) is prepared by saltification of the compound of formula 21 (0.42 gm) using hydrochloric acid at room temperature followed concentrated the filtrate under vacuum. (Yield=0.37 gm, 97.37%)

EXAMPLE 17

Analogously to example 1, {2-[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-ethyl}-carbamic acid tert-butyl ester (Formula 23) is prepared by the reaction of compound having formula 4 (1 gm) and 2-tert-Butoxycarbonylamino-propionic acid (0.464 gm). The residue was purified by silica gel chromatography using $CH_2Cl_2$/MeOH (9.5: 0.5) as an eluent. (Yield=0.91 gm, 65%)

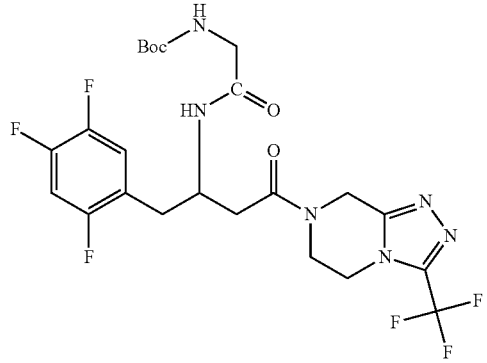

Formula 23

{[3-Oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-methyl}-carbamic acid tert-butyl ester

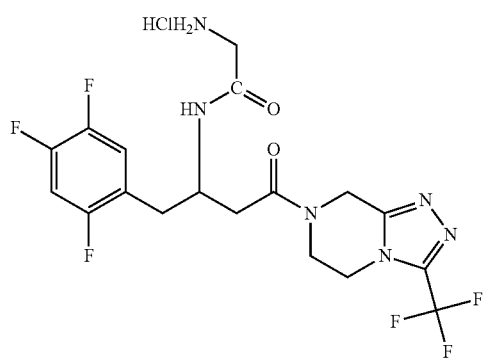

Formula 24

2-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-acetamide Hydrochloride

EXAMPLE 18

Analogously to example 2, 3-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide Hydrohloride (Formula 24) is prepared by saltification of the compound of formula 23 (0.89 gm) using hydrochloric acid at room temperature followed concentrated the filtrate under vacuum. (Yield: 0.78 gm, 98.73%)

EXAMPLE 19

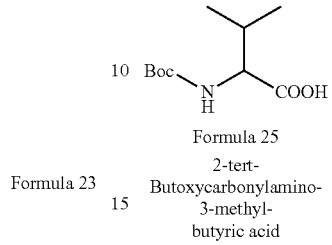 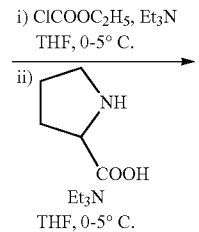

Formula 25
2-tert-Butoxycarbonylamino-3-methyl-butyric acid

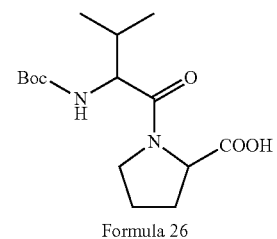

Formula 26
1-(2-tert-Butoxycarbonylamino-3-methyl-butyryl)-pyrrolidine-2-carboxylic acid To a stirred solution of 2-tert-Butoxycarbonylamino-3-methyl-butyric acid (Compound of formula 25) [8 gm, 0.037 mole] and tri ethyl amine (5.15 ml, 0.037 mole) in THF (120 ml), ethyl chloro formate (3.52 ml, 0.037 mole) was added drop wise at 0-5° C. The reaction was stirred at 0° C. for 15 minutes and stirred at room temperature for 1 hour. Then keep the reaction at 0° C. and add mixture of tri ethyl amine (10.3 ml, 0.074 mole) and THF (60 ml).

Finally L-Proline (4.25 gm, 0.037 mole) was added to above mixture at 0° C. Reaction was stirred at 0° C. for 30 minutes and stirred at room temperature for over night. After being stirred, THF was concentrated under vacuum and residue was acidified with 1N HCl (till pH ~3). The product layer was extracted with ethyl acetate. The organic extracts were dried over $Na_2SO_4$ and concentrated. The resulted product was subjected to column chromatography using EtoAC/Hexane 5/5 as an eluent to give 1-(2-tert-Butoxycarbonylamino-3-methyl-butyryl)-pyrrolidine-2-carboxylic acid (Formula 26). (Yield=3.6 gm, 31%)

EXAMPLE 20

To a stirred solution of 1-(2-tert-Butoxycarbonylamino-3-methyl-butyryl)-pyrrolidine-2-carboxylic acid (Formula 26) (0.39 gm, 1.23 mmol) in MDC (40 ml), dicyclohexyl dicarbobiimide (0.4 gm, 0.0019 mole) was added at 0° C., the reaction mixture was stirred for 5-10 minutes at 0° C. Then 3-Amino-1-(3-trifluoromethyl-5,6,7,8-tetrahydro-[1,2,4] triazolo[4,3-a]pyridin-7-yl)-4-(2,4,5-trifluoro-phenyl)-butan-1-one (0.5 gm, 0.00123 mole) was added to this mixture at 0° C. Then reaction was stirred at room temperature for 4 hours. Take the TLC for the completion of reaction. Reaction mixture was filtered to remove urea derivative of DCC. Then filtrate was concentrated in vacuum. Take the column chromatography of this compound for purification using $CHCl_3$/MeOH (9/1) as a solvent system to give (2-Methyl-1-{2-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carbonyl}-propyl)-carbamic acid tert-butyl ester (Compound of formula 27) [0.54 gm, 62% yield].

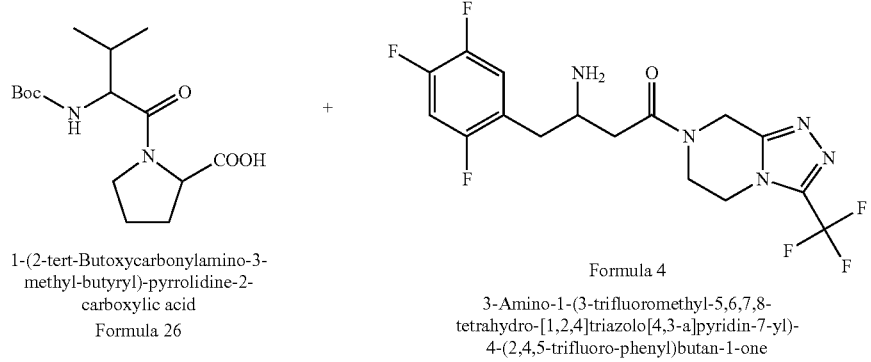

1-(2-tert-Butoxycarbonylamino-3-methyl-butyryl)-pyrrolidine-2-carboxylic acid
Formula 26

Formula 4
3-Amino-1-(3-trifluoromethyl-5,6,7,8-tetrahydro-[1,2,4]triazolo[4,3-a]pyridin-7-yl)-4-(2,4,5-trifluoro-phenyl)butan-1-one

DCC, MDC | 0° C.

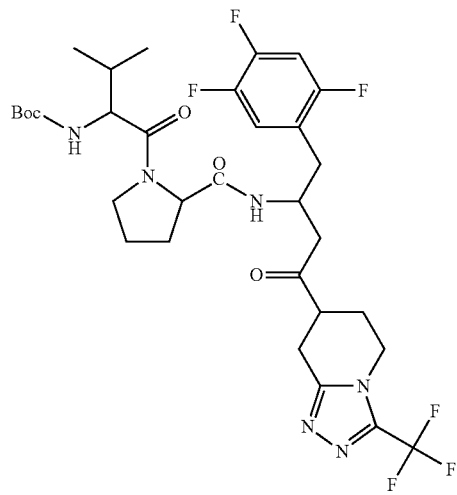

Formula 27

(2-Methyl-1-{2-[3-oxo-1-(2,4,5-trifluoro-benzyl)-3-(3-trifluoromethyl-5,6,7,8-tetrahydro-[1,2,4]triazolo[4,3-a]pyridin-7-yl)-propylcarbamoyl]-pyrrolidine-1-carbonyl}-propyl)-carbamic acid tert-butyl ester

EXAMPLE 21

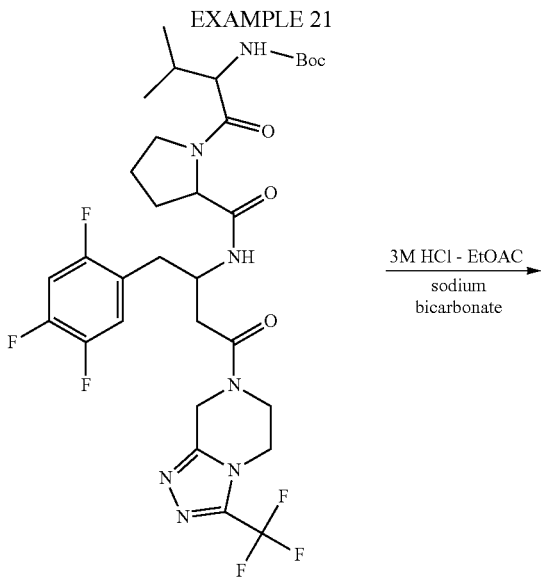

(2-Methyl-1-{2-[3-oxo-1-(2,4,5-trifluoro-benzyl)-
3-(3-trifluoromethyl-5,6-dihydro-8H-[1,2,4]triazolo
[4,3-a]pyrazin-7-yl)-propylcarbamoyl]-
pyrrolidine-1-carbonyl}-propyl)-carbamic acid
tert-butyl ester Formula 27

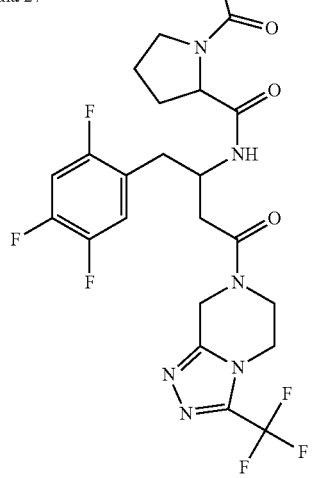

1-(2-Amino-3-methyl-butyryl)-pyrrolidine-
2-carboxylicacid[3-oxo-1-(2,4,5-trifluoro-benzyl)-3-(3-
trifluoromethyl-5,6-dihydro-8H-[1,2,4]
triazolo[4,3-a]pyrazin-7-yl)-propyl]-amide Formula 28

To a stirred solution of (2-Methyl-1-{2-[3-oxo-1-(2,4,5-trifluoro-benzyl)-3-(3-trifluoromethyl-5,6-dihydro-8H-[1,2,4]triazolo[4,3-a]pyrazin-7-yl)-propylcarbamoyl]-pyrrolidine-1-carbonyl}-propyl)-carbamic acid tert-butyl ester (Formula 27) (0.54 gm, 0.00077 mole) in ethyl acetate (5 ml), solution of 3M HCl in ethyl acetate (5 ml) was added at room temperature. Then reaction was stirred at room temperature for 1 hour. Take the TLC for the completion of reaction.

Then finally, reaction mixture was concentrated in vacuum to give Hydrochloride salt of 1-(2-Amino-3-methyl-butyryl)-pyrrolidine-2-carboxylic acid [3-oxo-1-(2,4,5-trifluoro-benzyl)-3-(3-trifluoromethyl-5,6-dihydro-8H-[1,2,4]triazolo[4,3-a]pyrazin-7-yl)-propyl]-amide. Thus obtain hydrochloric acid salt of compound is treated with sodium bicarbonate to give corresponding free base compound of formula 28. [0.46 gm, 93.88% yield]

EXAMPLE 22

Process for the preparation of 3-[2-(2-Amino-3-phenyl-propylamino)-2-(3-hydroxy-adamantan-1-yl)-acetyl]-3-aza-bicyclo-[3.1.0]-hexane-2-carbonitrile trifluoro acetic acid (Compound of formula 29)

Step A: The tert-Butoxycarbonylamino-(3-hydroxy-adamantan-1-yl)-acetic acid (13.56 gm, 0.0418 moles) and 3-Aza-bicyclo[3.1.0]hexane-2-carboxylic acid amide methane sulfonic acid (9.3 gm, 0.0418 moles) in ACN were stirred and added with stirring to the mixture of HoBT and DIPEA at room temperature. The above stirred solution was added into EDC.HCl at 0° C. followed by the addition of DIPEA and was stirred over 12 Hrs at room temperature. The acetonitrile was evaporated and residue was taken into EtOAC. The EtOAC layer was washed with 1N HCl and saturated bi-carbonate solution. The saturated mixture was dried over $Na_2SO_4$ and concentrated in vacuum. The pure compound of formula 27 was obtained by Column chromatography using MeOH: $CH_2Cl_2$ (0.5: 9.5) as a mobile phase. (Yield: 13 gm)

Step B: 13 gm of [2-(2-Carbamoyl-3-aza-bicyclo[3.1.0]hex-3-yl)-1-(3-hydroxy-adamantan-1-yl)-2-oxo-ethyl]-carbamic acid tert-butyl ester (0.0300 moles) was taken into $CH_2Cl_2$ (30 ml) and trifluoroacetic acid (15 ml) was added to the solution at room temperature. The reaction mixture was stirred for 3 hours. Di-chloromethane was evaporated to give oily residue which on titration with $Et_2O$ to afford as the white solid having formula 27a). (Yield 13 gm)

(Compound of formula 27a)

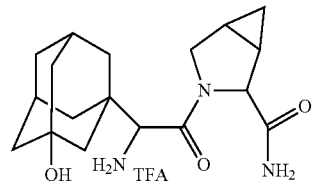

3-[2-Amino-2-(3-hydroxy-adamantan-1-yl)-
acetyl]-3-aza-bicyclo[3.1.0]hexane-2-carboxylic
acid amide trifluoro acetic acid Formula 33a

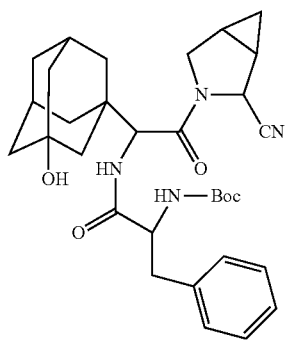

{1-[2-(2-Cyano-3-aza-bicyclo[3.1.0]hex-3-yl)-
1-(3-hydroxy-adamantan-1-yl)-2-oxo-
ethylcarbamoyl]-2-phenyl-ethyl]-carbamic
acid tert-butyl ester Scheme: 03

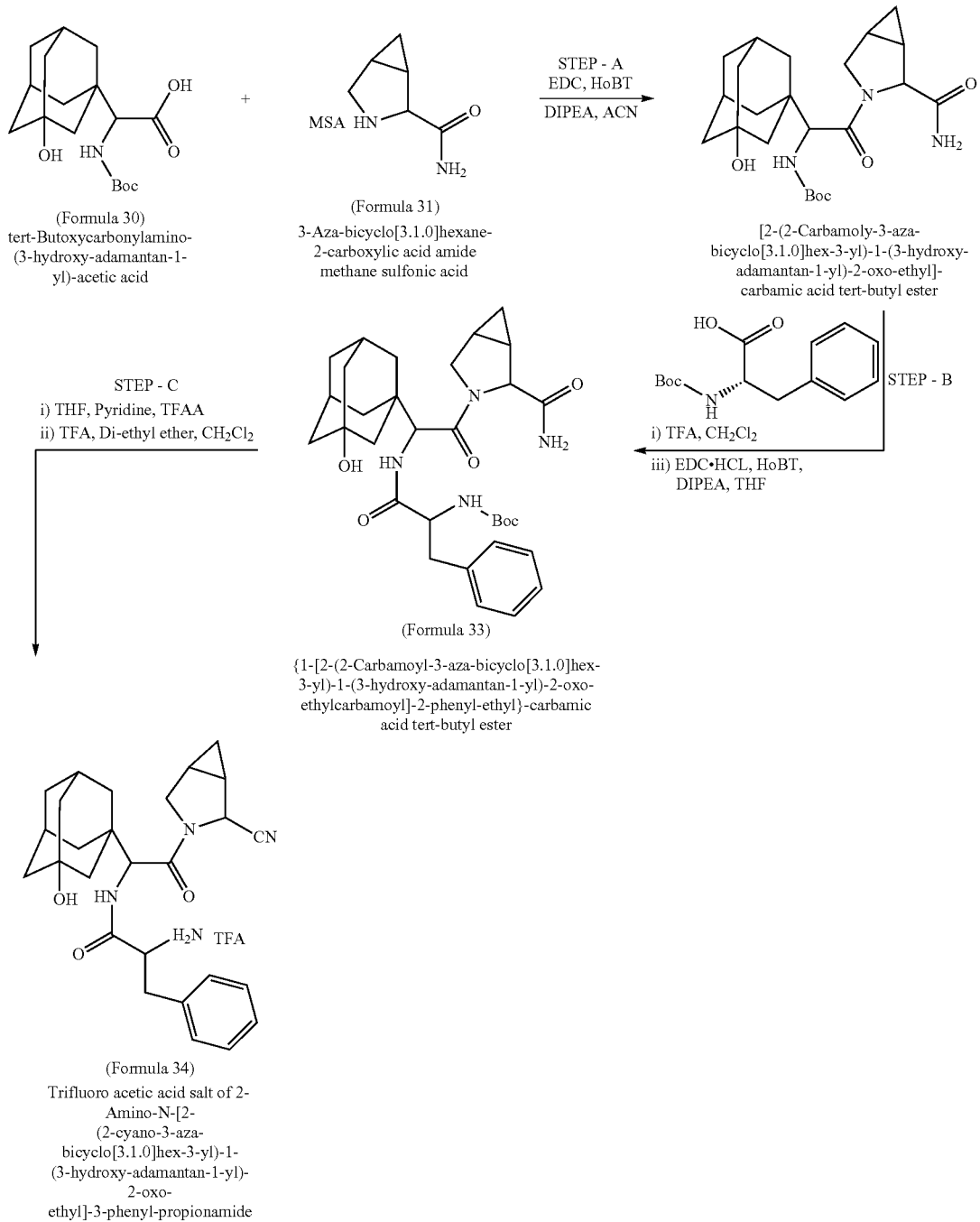

The solution of 2.27 gm (0.00507 moles) of compound 27a and 1.34 gm (0.00507 moles) of 2-tert-Butoxycarbonylamino-3-phenyl-propionic acid in TFA was added into HoBT (0.93 gm) and DIPEA (1.72 ml) at room temperature and stirred for 10 minutes. To this stirred solution EDC-HCl (1.2 gm) and DIPEA (1.76 ml) were added at 0° C. and the reaction mixture was stirred over 12 hrs at room temperature. THF was evaporated and residue was taken into EtOAC (40 ml). The EtOAC layer was washed with 1N HCl and aq. NaHCO$_3$, dried over Na$_2$SO$_4$ and concentrated in vacuum to give crude product. The crude product was purified by silica gel column chromatography using MeOH:CH$_2$Cl$_2$ (0.5: 9.5) as a mobile phase to give pure {1-[2-(2-Carbamoyl-3-aza-bicyclo[3.1.0]hex-3-yl)-1-(3-hydroxy-adamantan-1-yl)-2-oxo-ethylcarbamoyl]-2-phenyl-ethyl}-carbamic acid tert-butyl ester (Formula 33). [Yield: 1.5 gm]

Step C: 1.5 gm of {1-[2-(2-Carbamoyl-3-aza-bicyclo[3.1.0]hex-3-yl)-1-(3-hydroxy-adamantan-1-yl)-2-oxo-ethylcarbamoyl]-2-phenyl-ethyl}-carbamic acid tert-butyl ester of formula 33 (0.0031 moles) in THF was added into the mixture of pyridine (1.26 ml). Trifluoro acetic anhydride (10 ml) was added at 0° C. and stirred for 3 hours at room temperature. THF was evaporated and residue was taken into MeOH (30 ml) and 10 ml 10% $K_2CO_3$ solution was added. The reaction mixture is further stirred at room temperature for 3 hours. MeOH was evaporated and aq. layer was extracted with EtoAC. The combined EtoAC layers were washed with 1N HCl and bi-carbonate solution, dried over sodium sulphate and concentrated in vacuum to get crude product. The crude product was purified by silica gel column chromatography using MeOH:$CH_2Cl_2$ (9.8: 0.2) as a mobile phase to get pure compound of formula 33a. (Yield: 0.8 gm) 0.8 gm of compound of formula 33a (0.0014 moles) was added to a mixture of $CH_2Cl_2$ (10 ml) and trifluoro acetic acid (5 ml) at room temperature and stirred for 3 hours. After being stirred $CH_2Cl_2$ was evaporated and di-ethyl ether was added to remaining residue to afford white solid Trifluoro acetic acid salt of 2-Amino-N-[2-(2-cyano-3-aza-bicyclo[3.1.0]hex-3-yl)-1-(3-hydroxy-adamantan-1-yl)-2-oxo-ethyl]-3-phenyl-propionamide (Formula 34). (Yield: 0.8 gm)

EXAMPLE 23

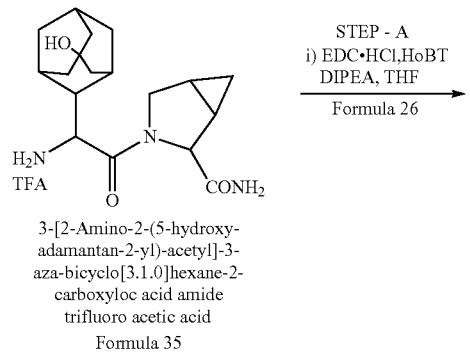

3-[2-Amino-2-(5-hydroxy-adamantan-2-yl)-acetyl]-3-aza-bicyclo[3.1.0]hexane-2-carboxyloc acid amide trifluoro acetic acid
Formula 35

STEP - A
i) EDC·HCl,HoBT DIPEA, THF
Formula 26

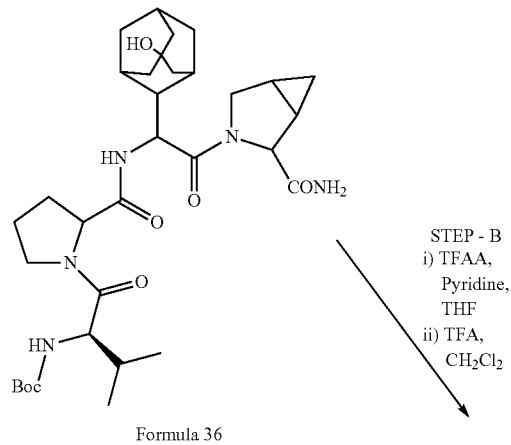

Formula 36
(1-{2-[2-(2-Carbamoyl-3-aza-bicyclo[3.1.0]hex-3-yl)-1-(5-hydroxy-adamantan-2-yl)-2-oxo-ethylcarbamoyl]-pyrrolidine-1-carbonyl}-2-methyl-propyl)-carbamic acid tert-butyl ester STEP - B
i) TFAA, Pyridine, THF
ii) TFA, $CH_2Cl_2$

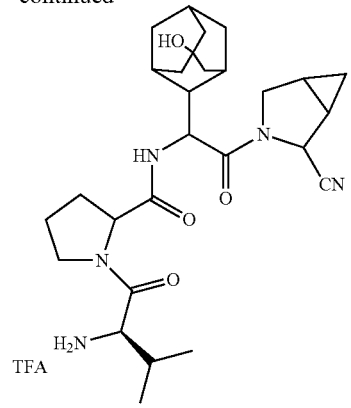

Formula 37
Trifluoro acetic acid salt of 1-(2-Amino-3-methyl-butyryl)-pyrrolidine-2-carboxylic acid [2-(2-cyano-3-aza-bicyclo[3.1.0]hex-3-yl)-1-(5-hydroxy-adamantan-2-yl)-2-oxo-ethyl]-amide To the stirred solution 1.7 gm (0.00380 moles) of 3-[2-Amino-2-(5-hydroxy-adamantan-2-yl)-acetyl]-3-aza-bicyclo[3.1.0]hexane-2-carboxylic acid amide trifluoro acetic acid of formula 35 and 1.19 gm (0.00380 moles) of 1-(2-tert-Butoxycarbonylamino-3-methyl-butyryl)-pyrrolidine-2-carboxylic acid (Formula 26) in THF was added into HoBT (0.6 gm) and DIPEA (1.3 ml) at room temperature and stirred for 10 minutes. To this stirred solution EDC.HCl (0.94 gm) and DIPEA (1.10 ml) were added at 0° C. and the reaction mixture was stirred over night at room temperature. THF was evaporated and residue was taken into EtOAC. The EtOAC layer was washed with 1N HCl and aq. $NaHCO_3$ solution, dried and concentrated in vacuum to get crude product. The crude product was purified by silica gel column chromatography to get pure (1-{2-[2-(2-Carbamoyl-3-aza-bicyclo[3.1.0]hex-3-yl)-1-(5-hydroxy-adamantan-2-yl)-2-oxo-ethylcarbamoyl]-pyrrolidine-1-carbonyl}-2-methyl-propyl)-carbamic acid tert-butyl ester (Formula 36). (Yield: 1.7 gm)

Analogously to example 23 the solution of 1.7 gm of (2-{2-[2-(2-Carbamoyl-3-aza-bicyclo[3.1.0]hex-3-yl)-1-(5-hydroxy-adamantan-2-yl)-2-oxo-ethylcarbamoyl]-pyrrolidin-1-yl}-1-methyl-2-oxo-ethyl)-carbamic acid tert-butyl ester in THF was added into the mixture of pyridine (1.0 ml) and Trifluoro acetic anhydride (0.95 ml). The reaction mixture was stirred at room temperature. THF was evaporated and residue was taken into MeOH and 10 ml 10% $K_2CO_3$ solution was added. MeOH was evaporated and aq. layer was extracted with EtoAC. The combined EtoAC layers were washed with 1N HCl and aq. $NaHCO_3$, dried over sodium sulphate and concentrated in vacuum to give crude product. The crude product was purified by column chromatography to get pure Trifluoro acetic acid salt of 1-(2-Amino-3-methyl-butyryl)-pyrrolidine-2-carboxylic acid [2-(2-cyano-3-aza-bicyclo[3.1.0]hex-3-yl)-1-(5-hydroxy-adamantan-2-yl)-2-oxo-ethyl]-amide of formula 37. (Yield: 0.7 gm)

In view of the present scope of invention, additionally the following novel compounds were also synthesized by the process as exemplified in the specification. The synthesized compound were screened to check their hypoglycemic effect through in vivo screening using Sitagliptin, Saxagliptin and other commercially available compound as control. The structures of some of the compounds prepared as per process described in present invention are as under:

The amino acid analogue of 2-({6-[(3R)-3-substituted-aminopiperidin-1-yl]-3-methyl-2,4-dioxo-3,4-dihydro-pyrimidin-1(2H)-yl}methyl)-benzonitrile and pharmaceutically acceptable salts is synthesized as per the process exemplified in the specification are given in Table 1:

TABLE 1

Formula 2

| Sr. No. | —R₁ |
|---|---|
| 1 | (alanine-like: —C(O)—CH(NH₂)—CH₃) |
| 2 | (valine-like: H₂N—CH(iPr)—C(O)—) |
| 3 | (leucine-like: H₂N—CH(CH₂iPr)—C(O)—) |
| 4 | (proline: pyrrolidine-2-carbonyl, NH) |
| 5 | (isoleucine-like: H₂N—CH(sec-Bu)—C(O)—) |
| 6 | (threonine-like: H₂N—CH(CH(OH)CH₃)—C(O)—) |
| 7 | (H₂N—CH(CH₂-(3-benzyloxyphenyl))—C(O)—) |
| 8 | (β-alanine: H₂N—CH₂—CH₂—C(O)—) |

TABLE 1-continued

Formula 2

| Sr. No. | —R₁ |
|---|---|
| 9 | (phenylalanine-like: H₂N—CH(CH₂Ph)—C(O)—) |
| 10 | (Ala-Pro dipeptide) |
| 11 | (Leu-Pro dipeptide) |
| 12 | (Val-Pro dipeptide) |
| 13 | (Val-Ala dipeptide) |
| 14 | (Ala-Pro dipeptide) |
| 15 | (tyrosine: H₂N—CH(CH₂-(4-hydroxyphenyl))—C(O)—) |

TABLE 1-continued
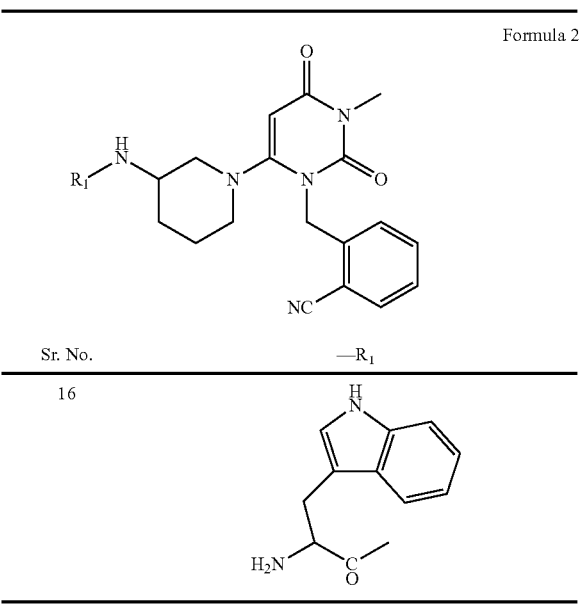
An amino acid analogue of 1-[2-Amino-3,3-bis-(4-fluoro-phenyl)-propionyl]-4-fluoro-pyrrolidine-2-carbonitrile and pharmaceutically acceptable salts is synthesized as per the process exemplified in the specification are given in Table 2.
TABLE 2
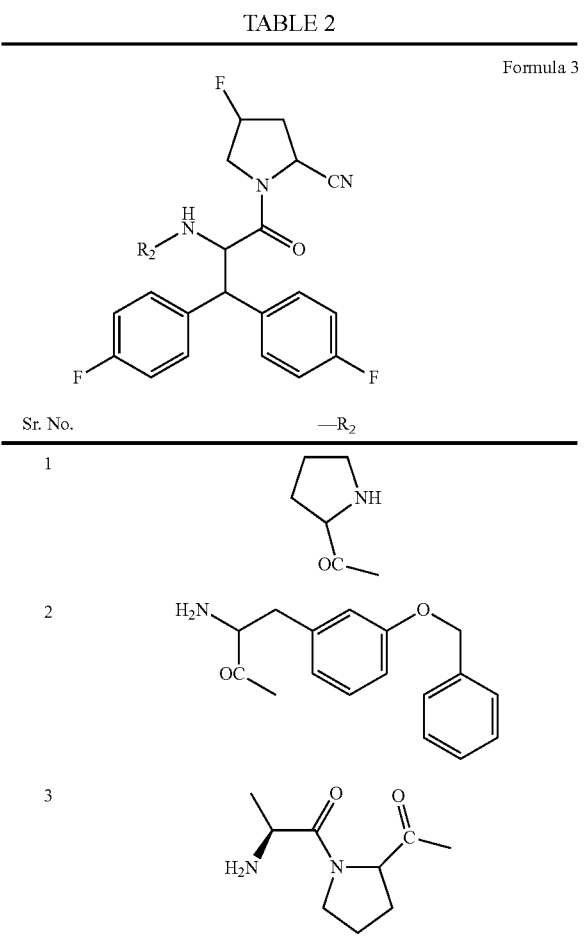
TABLE 2-continued
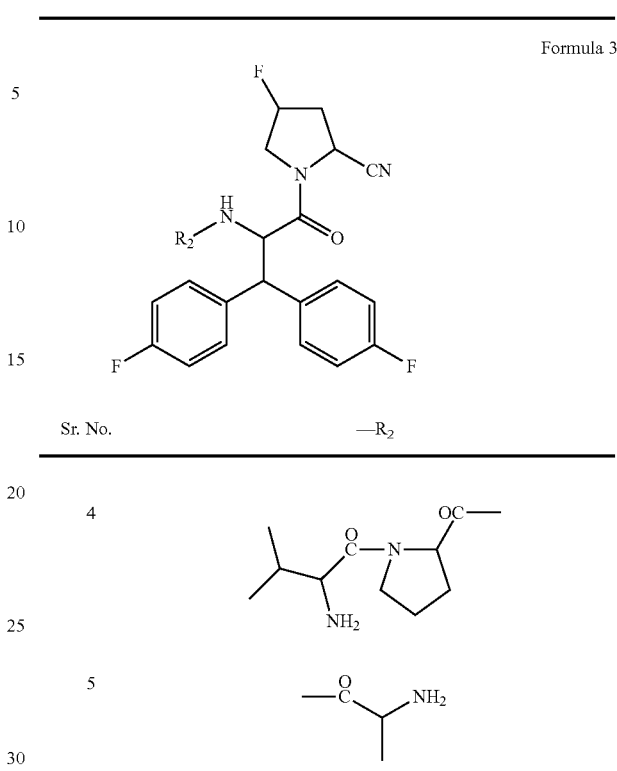

TABLE 2-continued

Formula 3

[Structure: 4-fluoropyrrolidine-2-carbonitrile connected via carbonyl to a carbon bearing NHR₂ and a CH group with two 4-fluorophenyl substituents]

| Sr. No. | —R₂ |
|---|---|
| 12 | [3-(1H-indol-3-yl)-2-aminopropanoyl, tryptophan-like] |
| 13 | [alaninyl-prolinyl methyl ester] |
| 14 | [phenylalanine methyl ester, H₂N-CH(CH₂Ph)-CO-OMe] |
| 15 | [bicyclic indolizidinone with amino and methoxycarbonyl substituents] |
| 16 | [tyrosine methyl ester, H₂N-CH(CH₂-C₆H₄-OH)-CO-OMe] |

An amino acid analogue of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and pharmaceutically acceptable salts is synthesized as per the process exemplified in the specification are given in Table 3

TABLE 3

Formula 4

[Structure: sitagliptin-like core with 2,4,5-trifluorophenyl group, CH₂, CH(NH-R₃), C(=O), connected to 3-(trifluoromethyl)-5,6-dihydro-[1,2,4]triazolo[4,3-a]pyrazin-7(8H)-yl]

| Sr. No. | —R₃ |
|---|---|
| 1 | [isoleucine methyl ester-like, H₂N-CH(CH(CH₃)CH₂CH₃)-CO-OMe] |
| 2 | [alanine methyl ester, -C(O)O-CH(CH₃)-NH₂] |
| 3 | [valine methyl ester, H₂N-CH(CH(CH₃)₂)-CO-OMe] |
| 4 | [prolinyl methyl ester] |
| 5 | [threonine methyl ester, H₂N-CH(CH(OH)CH₃)-CO-OMe] |
| 6 | [phenylalanine methyl ester, H₂N-CH(CH₂Ph)-CO-OMe] |
| 7 | [β-alanine methyl ester, H₂N-CH₂-CH₂-CO-OMe] |
| 8 | [leucine methyl ester, H₂N-CH(CH₂CH(CH₃)₂)-CO-OMe] |
| 9 | [tryptophan methyl ester, H₂N-CH(CH₂-indol-3-yl)-CO-OMe] |

TABLE 3-continued
Formula 4
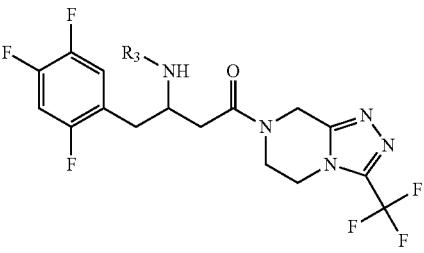
| Sr. No. | —R₃ |
|---|---|
| 10 | 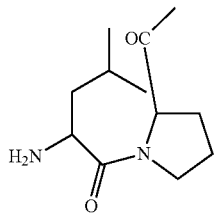 |
| 11 | 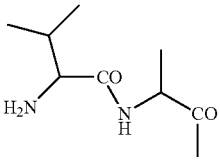 |
| 12 | 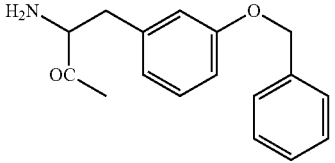 |
| 13 | 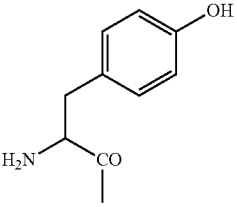 |
| 14 | 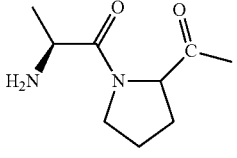 |
| 15 | 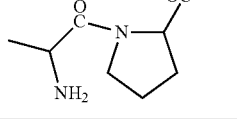 |
| 16 | 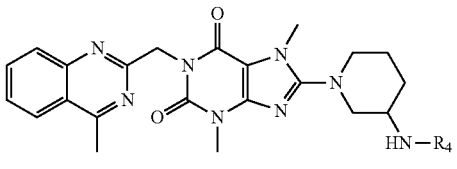 |
An amino acid analogue of 8-[(3R)-3-aminopiperidin-1-yl]-7-(but-2-yn-1-yl)-3-methyl-1-[(4-methylquinazolin-2-yl)methyl]-3,7-dihydro-1H-purine-2,6-dione and pharmaceutically acceptable salts is synthesized as per the process exemplified in the specification are given in Table 4:
TABLE 4
Formula 5
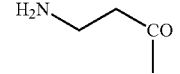
| Sr. No. | —R₄ |
|---|---|
| 1 | 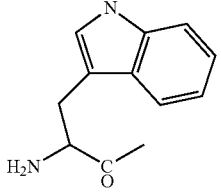 |
| 2 | 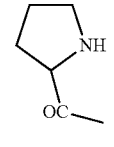 |
| 3 | 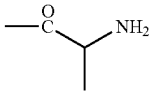 |
| 4 | 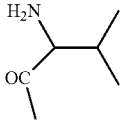 |
| 5 | 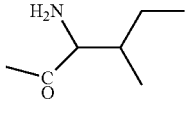 |
| 6 | 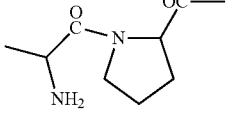 |
| 7 | 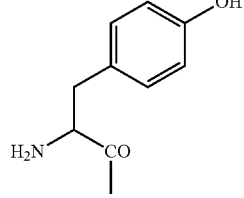 |
| 8 |  |

TABLE 4-continued
Formula 5
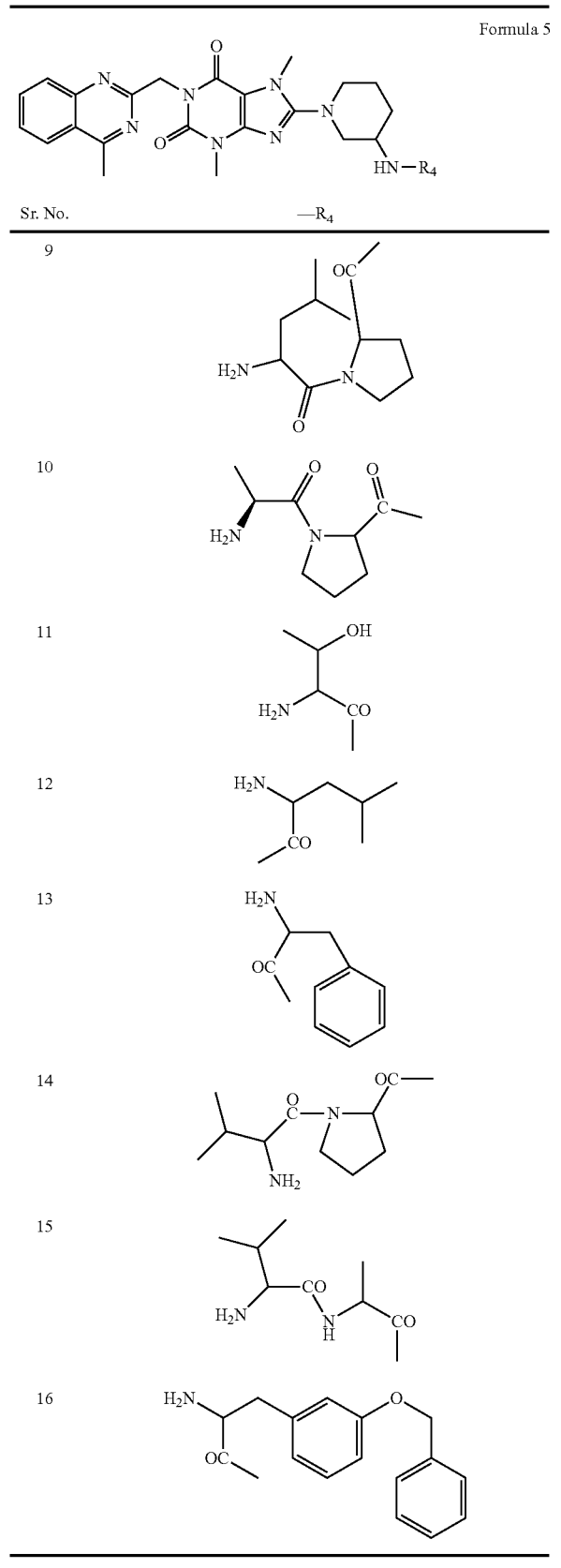
[3.1.0]-hexane-3-carbonitrile and pharmaceutically acceptable salts is synthesized as per the process exemplified in the specification are given in Table 5:
TABLE 5
Formula 6
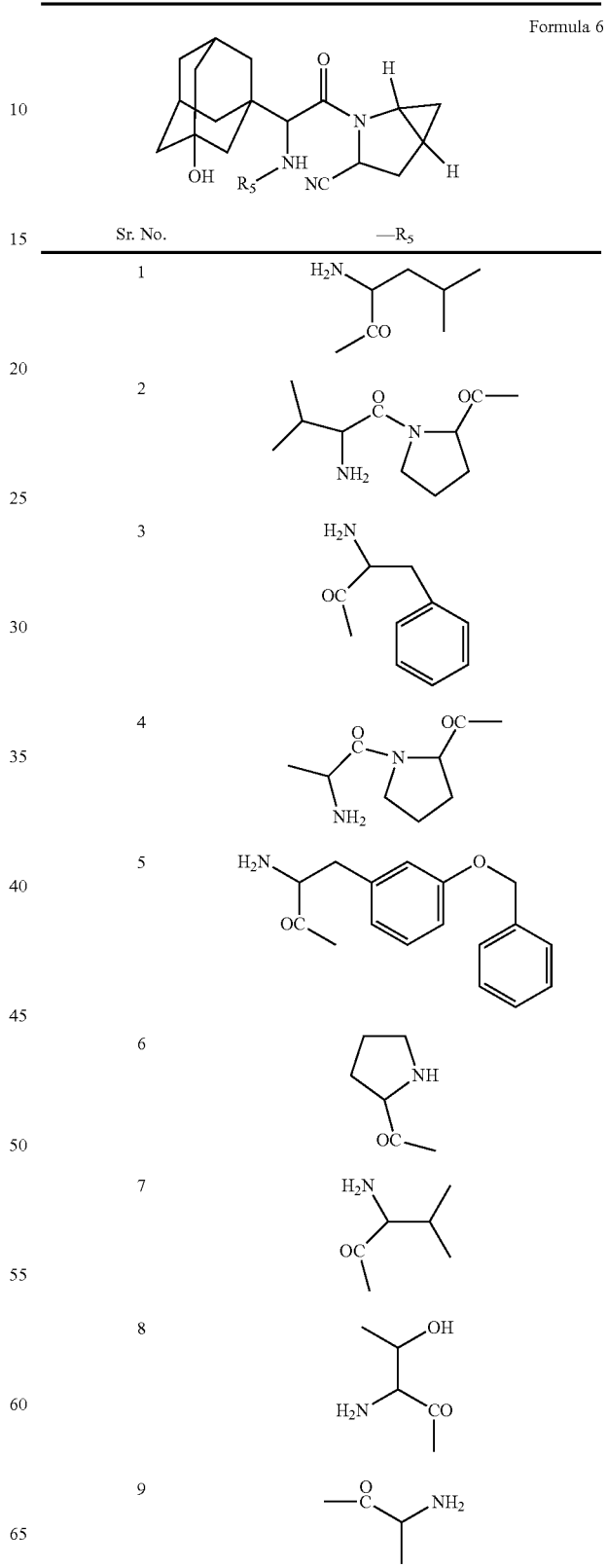
An amino acid analogue of (1S,3S,5S)-2-[(2S)-2-amino-2-(3-hydroxy-1-adamantyl)acetyl]-2-azabicyclo- TABLE 5-continued Formula 6

| Sr. No. | —R5 |
|---|---|
| 10 | (structure) |
| 11 | (indole-containing amino acid structure) |
| 12 | (bicyclic structure with H2N) |
| 13 | (H2N with branched chain) |
| 14 | (H2N-CH2-CH2-CO structure) |
| 15 | (dipeptide-like structure) |
| 16 | (tyrosine-like structure with OH phenyl) |

The novel hypoglycemic compounds according to present invention on reaction with DPP IV enzyme release an entity that inhibits the DPP IV enzyme. The inhibition of DPP IV enzyme by compound of formula 1 is attributed to the particular amino acid analogues synthesized as per present invention. These are evaluated by the in vivo screening of the compounds of present invention.

In Vivo Study of Synthesized Compounds:

The efficacy compound CPL-2009-0030 and CPL-2009-0031 were prepared as per present invention. They were evaluated through Oral Glucose Tolerance Test in animals. Each group consist of 10-12 weeks old Wistar female rats. The animals were divided into 4 different groups of 6 animals per group. The group I received vehical (WFI Placebo), Group II received Sitagliptin as positive control, Group III received CPL-2009-0030 and Group IV received CPL-2009-0031. All animals had over night fasting.

TABLE 01

Dose groups, no. of animals and dose of drugs for in vivo study:

| Group | No. of animals | Drugs | Equimolar Dose (In mg/kg) | Dose volume (mL/kg) |
|---|---|---|---|---|
| I | 6 | Vehicle (WFI) | 0.0 | 10 |
| II | 6 | Standard | 9.0 | 10 |
| III | 6 | CPL-2009-0030 | 11.28 | 10 |
| IV | 6 | CPL-2009-0031 | 12.0 | 10 |

The drug was administrated as per table 01 at 0 hour to all the study group animals with 10 mL/kg of dose volume. The compounds were administered orally. The glucose (2 gm/Kg body weight) was administered 3 hrs after the administration of compounds. Blood glucose was measured at the time of administration of compound, glucose and 30 min, 1 hr, 2 hr, 3 hr and 4 hr after the glucose administration. The change in glucose levels over time is shown in FIG. 1. All animals showed rise in blood glucose level following administration of glucose. The rise was maximum at 30 min after glucose administration. The rise in glucose is significantly lower when compound of present invention were administered compared to no treatment group. The difference between no treatment group and other three groups is maximum at 30 min and it decreases over time (FIG. 1). The findings also show that the compound of present invention does not alter the fasting glucose levels from 0 to 3 Hrs. Thus, the compound of present invention reduces hyperglycaemic effect of glucose without inducing hypoglycaemia. In other words, compounds of present invention provide hypoglycaemic effect only to reduce post-prandial hyperglycaemia without inducing fasting hypoglycaemia.

To confirm the finding the experiment was repeated three times and the percentage change in glucose level over time of three experiments is presented in table 02. The repeat experiments also confirm the findings.

TABLE 02

In vivo results of novel hypoglycaemic compounds

| Name of compound | % change in glucose level (Mean ± SEM) | | |
|---|---|---|---|
| | 30 Min | 1 Hr | 2 hr |
| No treatment | 199 ± 5 | 154 ± 4 | 122 ± 5 |
| Sitagliptin | 149 ± 5 | 130 ± 4 | 109 ± 2 |
| CPL-2009-0030 | 145 ± 13 | 127 ± 6 | 108 ± 5 |
| CPL-2009-0031 | 125 ± 3 | 123 ± 4 | 110 ± 3 |

Similarly in identical experiments were performed to evaluate the in vivo screening of compounds as per present invention. The result of in vivo screening for evaluation of hypoglycemic effect of CPL-2009-0011, CPL-2009-0012, CPL-2009-0015 and CPL-2009-0020 are given in FIG. 2. The result of in vivo screening for evaluation of hypoglycemic effect against Saxagliptin as control compound for CPL-2010-0079, CPL-2010-0085 is given in FIG. 3 whereas the same compound were screened against sitagliptin control and results are given in FIG. 4.

The above results indicate that the newly synthesized compounds are showing hypoglycemic activity as compared to standard. The novel hypoglycemic compounds according to present invention on reaction with DPP IV enzyme release an entity that inhibits the DPP IV enzyme. This is further evaluated by following analytical method.

Analytical Method to Analyze the DPP IV Compounds of Present Invention:

Reagents and Solvents: The reagents, solvents, standards and equipments to analyze the DPP IV compounds of present invention are as under:

Trifluoro Acetic acid (AR grade)
    Acetonitrile (HPLC grade)
    Milli Q water
    Sitagliptin Base as working standard DPP IV inhibitor
    Shimadzu LC-2010 equipped with UV detector and Auto Sampler
    Diluent: Acetonitrile Preparation of Buffer Transfer accurately measured 1000 mL Milli Q water in a beaker. Adjust pH 2.00±0.05 with Trifluoro acetic acid. Shake it gently and filter through 0.45µ membrane filter.

Preparation of Mobile Phase

Transfer 300 mL acetonitrile in 1000 mL volumetric flask and make the volume up to the mark with buffer pH 2.00±0.05

Standard Preparation

Exactly weigh about 20 mg Sitagliptin Base working standard in 10 mL volumetric flask. Add 5.0 mL diluent and sonicate it (if required) to dissolve the solids and make the volume up to the mark with diluent giving a standard solution having concentration 2000 ppm (Stock solution).

Above stock solution was further diluted to get different concentration solution varying from 0.025 µM to 100 µM. Linearity curve of peak area against concentration in µM was plotted for different concentration.

Sample Preparation

Extracted samples (after removing proteneous matter) were provided from different organs (Liver, Kidney and Pancreas) and serum samples which were directly injected on to HPLC system.

Chromatographic Conditions:

The liquid chromatography is equipped with variable wavelength UV detector, Auto sampler and Data processor
    Column: ypersil BDS C8, 4.6 mm×250 mm, 5µ
    Detector wavelength: 54 nm
    Flow Rate: 1.0 mL/min
    Injection volume: 20 µL
    Column Temperature: 60° C.

Procedure

Inject blank (diluent) and blank extraction samples, inject standard preparation of varying concentration from 0.025 µM to 100 µM and plot a graph of Area under curve against concentration in µM. Inject sample preparation and record the chromatogram. Disregard any peak due to blank and calculate concentration of an entity which is released from the extracted samples collected at different time intervals. The retention time of Sitagliptine is about 5.0 to 6.0 minutes.

The following compounds are exemplified with non-limiting scope of the invention for their in vivo screening of the compound presented according to present invention. The results are discussed in relevant example and presented as FIG. 1-4.

CPL-2009-0011

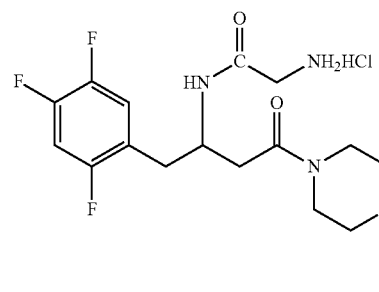

CPL-2009-0030

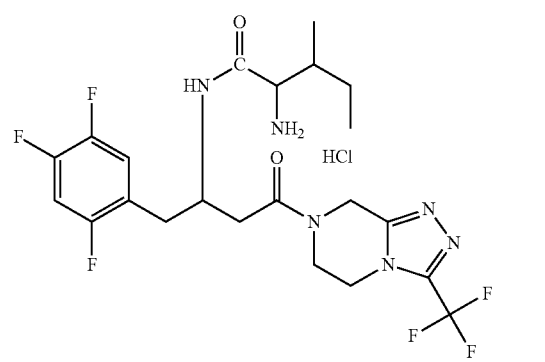

CPL-2009-0012

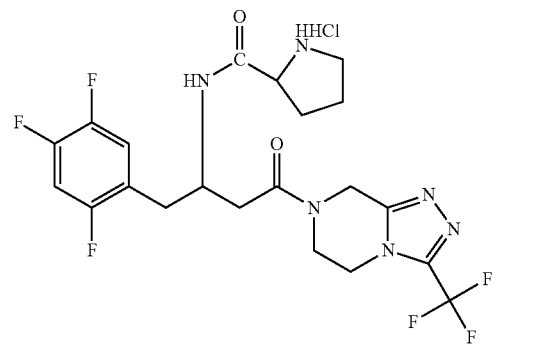

CPL-2009-0020

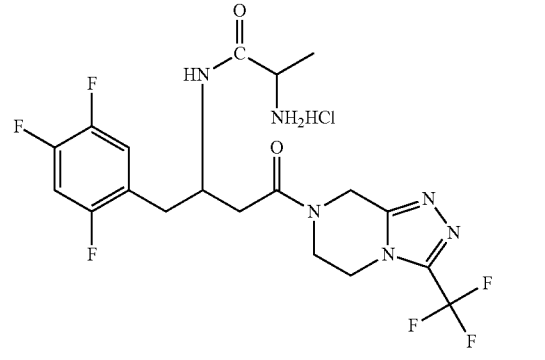

-continued

CPL-2009-0015

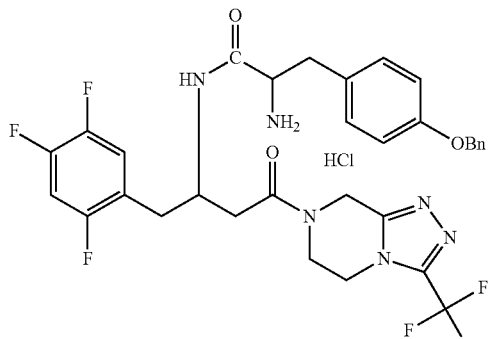

CPL-2009-0031

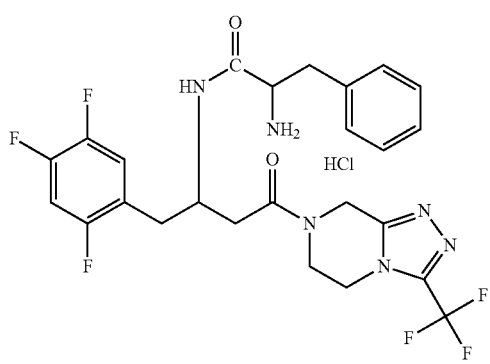

CPL-2009-0009

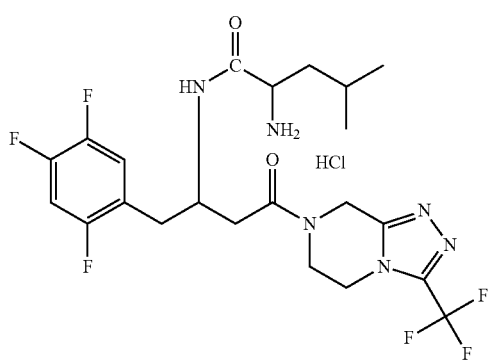

CPL-2009-0007

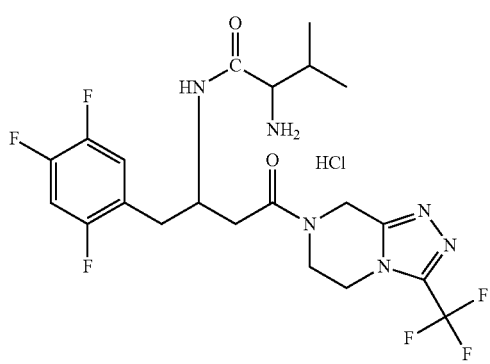

-continued

CPL-2010-0079

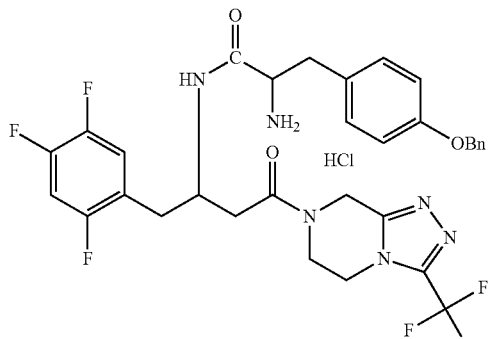

CPL-2011-0085

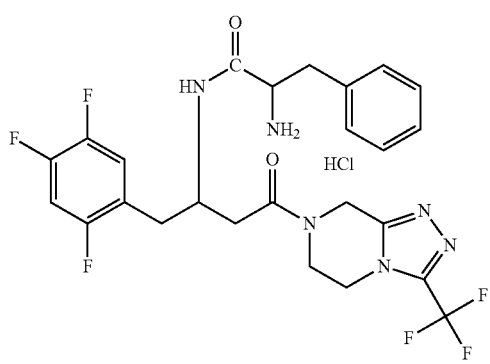

The novel hypoglycemic compounds of formula I and its pharmaceutically acceptable salts thereof according to present invention are showing hypoglycemic activity in vivo model comprising the pharmaceutical composition combining a compound of the present invention with a pharmaceutical carrier or diluent.

What is claimed is:

1. A compound of formula 1,

Formula 1

$$A\diagdown N \diagup H$$
$$\phantom{AAA}|$$
$$\phantom{AAA}R$$

wherein, A is an amino acid selected from glycine, alanine, β-alanine, valine, histidine, serine, leucine, isoleucine, phenylalanine, methionine, tryptophan, lysine, glutamine, glutamic acid, proline, cysteine, tyrosine, arginine, asparagine, aspartic acid, or threonine;

wherein R-NH- is selected from formulae 2 to 6:

Formula 2

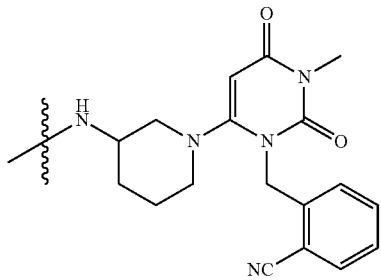

Formula 3

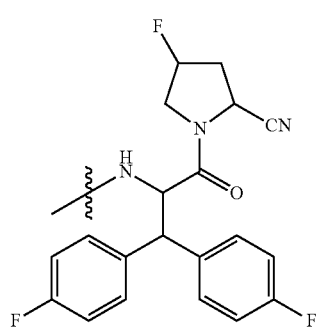

Formula 4

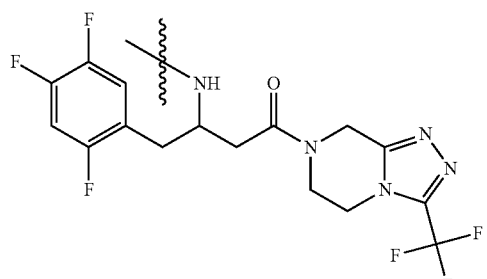

Formula 5

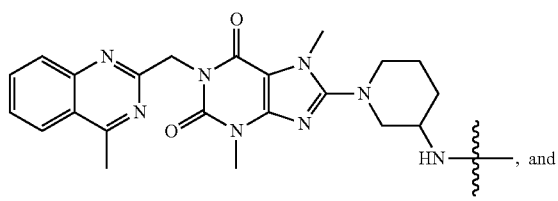, and

Formula 6

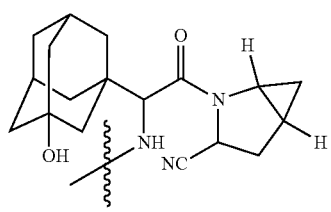

or a pharmaceutically acceptable salt thereof.

2. The compound of claim 1, wherein R-NH- is formula 2, or a pharmaceutically acceptable salt thereof.

3. The compound of claim 1, wherein R-NH- is formula 3, or a pharmaceutically acceptable salt thereof.

4. The compound of claim 1, wherein R-NH- is formula 4, or a pharmaceutically acceptable salt thereof.

5. The compound of claim 1, wherein R-NH- is formula 5, or a pharmaceutically acceptable salt thereof.

6. The compound of claim 1, wherein R-NH- is formula 6, or a pharmaceutically acceptable salt thereof.

7. A compound selected from:

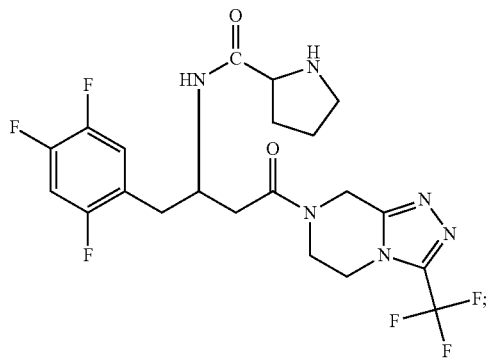

Pyrrolidine-2-carboxylic acid [3-oxo-1-(2,4,5-trifluoro-benzyl)-3-(3-trifluoromethyl-5,6-dihydro-8H-[1,2,4]triazol[4,3-a]pyrazin-7-yl)-propyl]amide

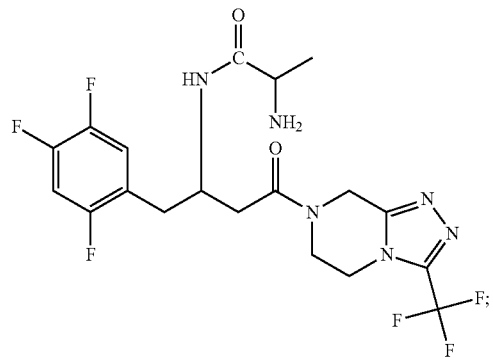

2-Amino-N-[3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-propionamide

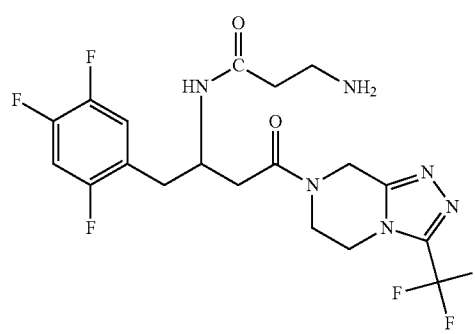

3-Amino-N-[3-oxo-1-(2,4,5-trifluoro-benzyl)-3-(3-trifluoromethyl-5,6-dihydro-8H-[1,2,4]triazolo[4,3-a]pyrazin-7-yl)-propyl]-propionamide -continued

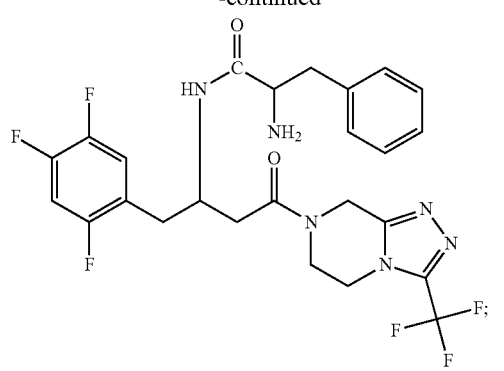

2-Amino-N-[3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-3-phenyl-propionamide

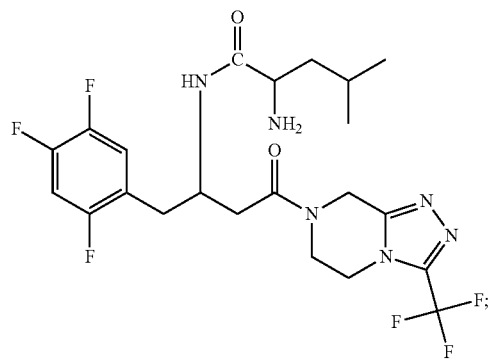

2-Amino-4-methyl-pentanoic acid [3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-amide

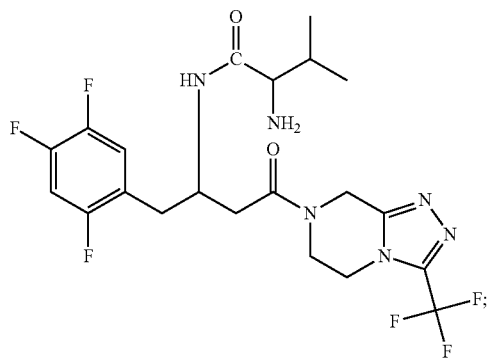

2-Amino-3-methyl-N-[3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-butyramide

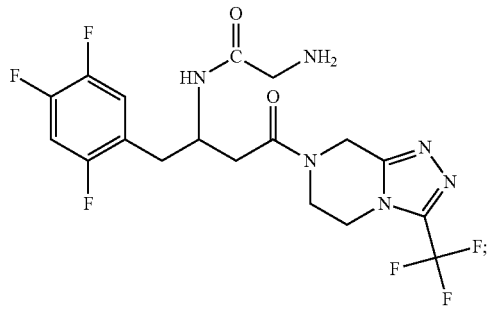

2-Amino-N-[3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-acetamide -continued

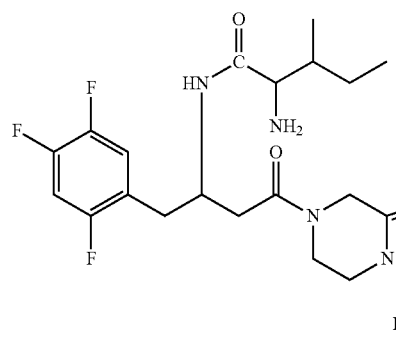

2-Amino-3-methyl-pentanoic acid [3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-amide

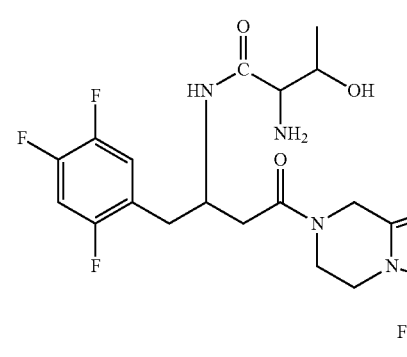

2-Amino-3-hydroxy-N-[3-oxo-1-(2,4,5-trifluoro-benzyl)-3-(3-trifluoromethyl-5,6-dihyrdo-8H-[1,2,4]triazolo[4,3-a]pyrazin-7-yl)-propyl]-butyramide or a pharmaceutically acceptable salt thereof.

8. A compound selected from:

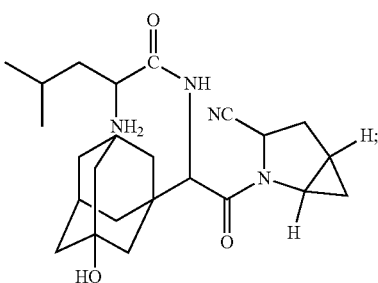

2-Amino-4-methyl-pentanoic acid [2-(3-cyano-2-aza-bicyclo[3.1.0]hex-2-yl)-1-(3-hydroxy-adamantan-1-yl)-2-oxo-ethyl]-amide -continued

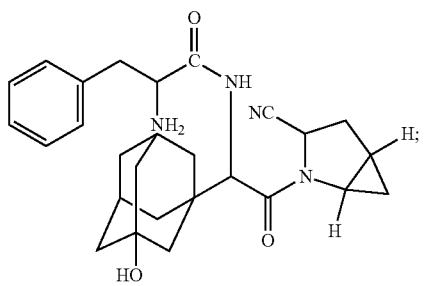

2-Amino-N-[2-(3-cyano-2-aza-bicyclo[3.1.0]hex-2-yl)-1-(3-hydroxy-adamantan-1-yl)-2-oxo-ethyl]-3-phenyl-propionamide

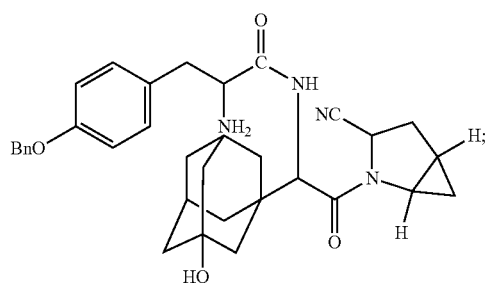

2-Amino-3-(benzyloxy-phenyl)-N-[2-(3-cyano-2-aza-bicyclo[3.1.0]hex-2-yl)-1-(3-hydroxy-adamantan-1-yl)-2-oxo-ethyl]-propionamide

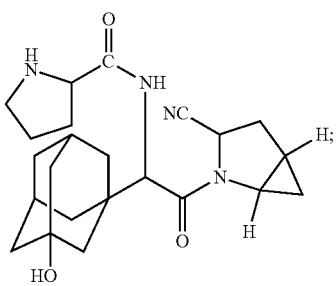

Pyrrolidine-2-carboxylic acid [2-(3-cyano-2-aza-bicyclo[3.1.0]hex-2-yl)-1-(3-hydroxy-adamantan-1-yl)-2-oxo-ethyl]-amid

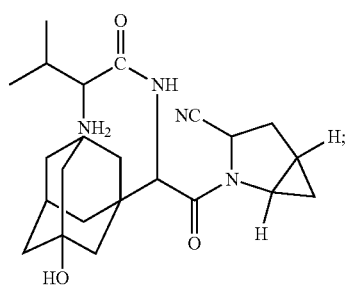

2-Amino-N-[2-(3-cyano-2-aza-bicyclo[3.1.0]hex-2-yl)-1-(3-hydroxy-adamantan-1-yl)-2-oxo-ethyl]-3-methyl-butyramide -continued

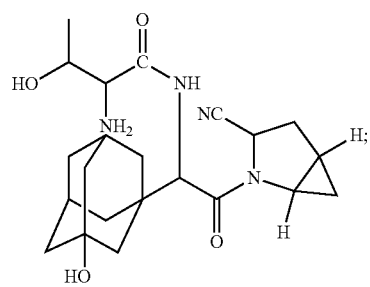

2-Amino-N-[2-(3-cyano-2-aza-bicyclo[3.1.0]hex-2-yl)-1-(3-hydroxy-adamantan-1-yl)-2-oxo-ethyl]-3-hydroxy-butyramide

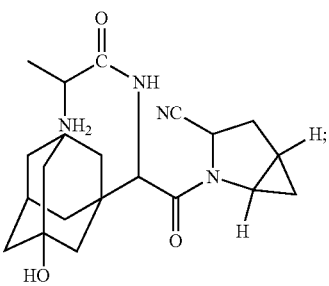

2-Amino-N-[2-(3-cyano-2-aza-bicyclo[3.1.0]hex-2-yl)-1-(3-hydroxy-adamantan-1-yl)-2-oxo-ethyl]-propionamide

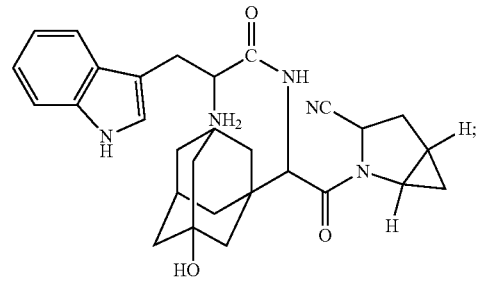

2-Amino-N-[2-(3-cyano-2-aza-bicyclo[3.1.0]hex-2-yl)-1-(3-hydroxy-adamantan-1-yl)-2-oxo-ethyl]-3-(1H-indol-3-yl)-propionamide

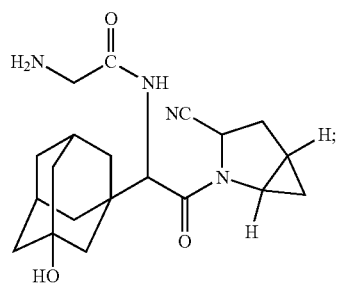

2-Amino-N-[2-(3-cyano-2-aza-bicyclo[3.1.0]hex-2-yl)-1-(3-hydroxy-adamantan-1-yl)-2-oxo-ethyl]-acetamide -continued
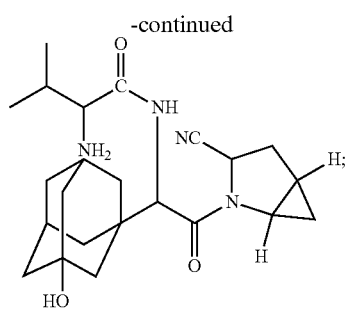
2-Amino-3-methyl-pentanoic acid [2-(3-cyano-2-aza-bicyclo[3.1.0]hex-2-yl)-1-(3-hydroxy-adamantan-1-yl)-2-oxo-ethyl]-amide
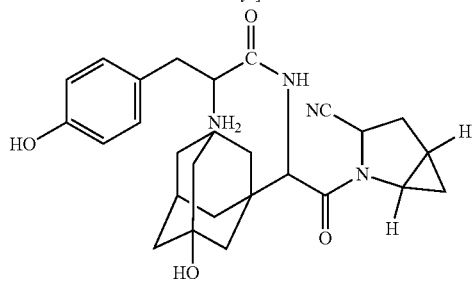
2-Amino-N-[2-(3-cyano-2-aza-bicyclo[3.1.0]hex-2-yl)-1-(3-hydroxy-adamantan-1-yl)-2-oxo-ethyl]-3-(4-hydroxy-phenyl)-propionamide
or a pharmaceutically acceptable salt thereof.
* * * * *